United States Patent
Fourage et al.

(10) Patent No.: US 10,407,638 B2
(45) Date of Patent: Sep. 10, 2019

(54) PRODUCTION OF ALPHA-OLEFINS

(71) Applicants: TOTAL RAFFINAGE CHIMIE, Courbevoie (FR); QINGDAO INSTITUTE OF BIOENERGY AND BIOPROCESS TECHNOLOGY (QIBEBT), Qindao Shandong (CN)

(72) Inventors: Laurent Fourage, Suresnes (FR); Frédéric Laeuffer, Paris (FR); Henri Strub, Pont Sainte Maxence (FR); Yun Wang, Qindao Shandong (CN); Jian Xu, Qindao Shandong (CN); Huifang Xu, Qindao Shandong (CN); Shengying Li, Qindao Shandong (CN)

(73) Assignees: Total Raffinage Chimie, Courbevoie (FR); Qingdao Institute of Bioenergy and Bioprocess Technology, Qindao, Shandong (CN)

( * ) Notice: Subject to any disclaimer, the term of this patent is extended or adjusted under 35 U.S.C. 154(b) by 0 days.

(21) Appl. No.: 15/737,326

(22) PCT Filed: Jun. 30, 2016

(86) PCT No.: PCT/EP2016/065389
§ 371 (c)(1),
(2) Date: Dec. 18, 2017

(87) PCT Pub. No.: WO2017/001606
PCT Pub. Date: Jan. 5, 2017

(65) Prior Publication Data
US 2018/0171252 A1    Jun. 21, 2018

(30) Foreign Application Priority Data
Jun. 30, 2015  (EP) .................... 15174554

(51) Int. Cl.
*C12N 9/88* (2006.01)
*C10M 105/04* (2006.01)
*C12P 5/02* (2006.01)

(52) U.S. Cl.
CPC ............ *C10M 105/04* (2013.01); *C12N 9/88* (2013.01); *C12P 5/026* (2013.01); *C07K 2319/21* (2013.01); *C10M 2203/024* (2013.01); *C10M 2205/0285* (2013.01); *C10N 2240/10* (2013.01); *C10N 2270/00* (2013.01)

(58) Field of Classification Search
CPC .................................. C10G 3/00; C12N 9/88
USPC ..................... 435/166, 252.3, 232
See application file for complete search history.

(56) References Cited

U.S. PATENT DOCUMENTS

| | | | |
|---|---|---|---|
| 8,597,922 B2 * | 12/2013 | Alibhai | C10G 3/00 435/167 |
| 2011/0196180 A1 | 8/2011 | Alibhai et al. | |
| 2012/0253088 A1 * | 10/2012 | Alibhai | C10G 3/00 585/16 |
| 2013/0130952 A1 | 5/2013 | Luo et al. | |

OTHER PUBLICATIONS

PCT International Search Report and Written Opinion dated Nov. 29, 2016 for PCT International Patent Application No. PCT/EP2016/065389, 16 pages.
Database UniProt [Online] May 27, 2015 (May 27, 2015), "SubName: Full=Cytochrome P450 family protein {ECO:0000313:EMBL:EKU50422.1};", XP002761949, retrieved from EBI accession No. UNIPROT: K9B6J8 Database accession No. K9B6J8, 1 page.
Database UniProt [Online] Feb. 10, 2009 (Feb. 10, 2009), "SubName: Full=Cytochrome P450 {ECO:0000313:EMBL:EED06866.1};", XP002764068, retrieved from EBI accession No. UNIPROT:B7DSS6 Database accession No. B7DSS6, 1 page.
Liu Y et al., "Hydrogen peroxide-independent production of ?-alkenes by OleTJE P450 fatty acid decarboxylase", Biotechnology for Biofuels, vol. 7, No. I, Feb. 24, 2014 (Feb. 24, 2014), XP021179059, 12 pages.
Rude M A et al., "Terminal Olefin (1-Alkene) Biosynthesis by a Novel P450 Fatty Acid Decarboxylase from Jeotgalicoccus Species", Applied and Environmental Microbiology, vol. 77, No. 5, Jan. 7, 2011 (Jan. 7, 2011), pp. 1718-1727, XP055231228.
Mendez-Perez D et al., "Modular synthase-encoding gene involved in [alpha]-olefin biosynthesis in Synechococcus sp. strain PCC 7002", Applied and Environmental Microbiology, vol. 77, No. 12, Apr. 29, 2011 (Apr. 29, 2011), pp. 4264-4267, XP002715053.

* cited by examiner

*Primary Examiner* — Tekchand Saidha
(74) *Attorney, Agent, or Firm* — Amster, Rothstein & Ebenstein LLP

(57) ABSTRACT

The present invention relates to the biosynthesis of α-olefins. In particular, the invention provides methods for the production of medium-chain α-olefins, more particularly $C_{11}$ α-olefins, using a polypeptide with decarboxylase activity on free fatty acids with 8 to 14 carbons, in particular on $C_8$-$C_{12}$ free fatty acids, more particularly on $C_{12}$ free fatty acids, or a genetically engineered host cell expressing or overexpressing said polypeptide.

18 Claims, 10 Drawing Sheets
Specification includes a Sequence Listing.

A) SEQ ID NO:1: *Jeotgalicoccus* sp. ATCC 8456 terminal olefin-forming fatty acid decarboxylase gene, complete cds ATGGCAACACTTAAGAGGGATAAGGGCTTAGATAATACTTTGAAAGTATTAAAGCAAGGTTATC
TTTACACAACAAATCAGAGAAATCGTCTAAACACATCAGTTTTCCAAACTAAAGCACTCGGTGG
TAAACCATTCGTAGTTGTGACTGGTAAGGAAGGCGCTGAAATGTTCTACAACAATGATGTTGTT
CAACGTGAAGGCATGTTACCAAAACGTATCGTTAATACGCTTTTTGGTAAAGGTGCAATCCATA
CGGTAGATGGTAAAAAACACGTAGACAGAAAAGCATTGTTCATGAGCTTGATGACTGAAGGTAA
CTTGAATTATGTACGAGAATTAACGCGTACATTATGGCATGCGAACACACAACGTATGGAAAGT
ATGGATGAGGTAAATATTTACCGTGAATCTATCGTACTACTTACAAAAGTAGGAACACGTTGGG
CAGGCGTTCAAGCACCACCTGAAGATATCGAAAGAATCGCAACAGACATGGACATCATGATCGA
TTCATTTAGAGCACTTGGTGGTGCCTTTAAAGGTTACAAGGCATCAAAAGAAGCACGTCGTCGT
GTTGAAGATTGGTTAGAAGAACAAATTATTGAGACTCGTAAAGGGAATATTCATCCACCAGAAG
GTACAGCACTTTACGAATTTGCACATTGGGAAGACTACTTAGGTAACCCAATGGACTCAAGAAC
TTGTGCGATTGACTTAATGAACACATTCCGCCCATTAATCGCAATCAACAGATTCGTTTCATTC
GGTTTACACGCGATGAACGAAAACCCAATCACACGTGAAAAAATTAAATCAGAACCTGACTATG
CATATAAATTCGCTCAAGAAGTTCGTCGTTACTATCCATTCGTTCCATTCCTTCCAGGTAAAGC
GAAAGTAGACATCGACTTCCAAGGCGTTACAATTCCTGCAGGTGTAGGTCTTGCATTAGATGTT
TATGGTACAACGCATGATGAATCACTTTGGGACGATCCAAATGAATTCCGCCCAGAAAGATTCG
AAACTTGGGACGGATCACCATTTGACCTTATTCCACAAGGTGGTGGAGATTACTGGACAAATCA
CCGTTGTGCAGGTGAATGGATCACAGTAATCATCATGGAAGAAACAATGAAATACTTTGCAGAA
AAAATAACTTATGATGTTCCAGAACAAGATTTAGAAGTGGACTTAAACAGTATCCCAGGATACG
TTAAGAGTGGCTTTGTAATCAAAAATGTTCGCGAAGTTGTAGACAGAACATAA

B) SEQ ID NO:2

MATLKRDKGLDNTLKVLKQGYLYTTNQRNRLNTSVFQTKALGGKPFVVVTGKEGAEMFYNNDVV
QREGMLPKRIVNTLFGKGAIHTVDGKKHVDRKALFMSLMTEGNLNYVRELTRTLWHANTQRMES
MDEVNIYRESIVLLTKVGTRWAGVQAPPEDIERIATDMDIMIDSFRALGGAFKGYKASKEARRR
VEDWLEEQIIETRKGNIHPPEGTALYEFAHWEDYLGNPMDSRTCAIDLMNTFRPLIAINRFVSF
GLHAMNENPITREKIKSEPDYAYKFAQEVRRYYPFVPFLPGKAKVDIDFQGVTIPAGVGLALDV
YGTTHDESLWDDPNEFRPERFETWDGSPFDLIPQGGGDYWTNHRCAGEWITVIIMEETMKYFAE
KITYDVPEQDLEVDLNSIPGYVKSGFVIKNVREVVDRT

FIG. 1

C) SEQ ID NO:3: *Bacillus subtilis* subsp. *subtilis* str. 168 chromosome, complete genome

```
ATGAATGAGCAGATTCCACATGACAAAAGTCTCGATAACAGTCTGACACTGCTGAAGGAAGGGT
ATTTATTTATTAAAAACAGAACAGAGCGCTACAATTCAGATCTGTTTCAGGCCCGTTTGTTGGG
AAAAAACTTTATTTGCATGACTGGCGCTGAGGCGGCGAAGGTGTTTTATGATACGGATCGATTC
CAGCGGCAGAACGCTTTGCCTAAGCGGGTGCAGAAATCGCTGTTTGGTGTTAATGCGATTCAGG
GAATGGATGGCAGCGCGCATATCCATCGGAAGATGCTTTTCTGTCATTGATGACACCGCCGCA
TCAAAAACGTTTGGCTGAGTTGATGACAGAGGAGTGGAAAGCAGCAGTCACAAGATGGGAGAAG
GCAGATGAGGTTGTGTTATTTGAAGAAGCAAAAGAAATCCTGTGCCGGGTAGCGTGCTATTGGG
CAGGTGTTCCGTTGAAGGAAACGGAAGTCAAAGAGAGAGCGGATGACTTCATTGACATGGTCGA
CGCGTTCGGTGCTGTGGGACCGCGGCATTGGAAAGGAAGAAGAGCAAGGCCGCGTGCGGAAGAG
TGGATTGAAGTCATGATTGAAGATGCTCGTGCCGGCTTGCTGAAAACGACTTCCGGAACAGCGC
TGCATGAAATGGCTTTTCACACACAAGAAGATGGAAGCCAGCTGGATTCCCGCATGGCAGCCAT
TGAGCTGATTAATGTACTGCGGCCTATTGTCGCCATTTCTTACTTTCTGGTGTTTTCAGCTTTG
GCGCTTCATGAGCATCCGAAGTATAAGGAATGGCTGCGGTCTGGAAACAGCCGGGAAAGAGAAA
TGTTTGTGCAGGAGGTCCGCAGATATTATCCGTTCGGCCCGTTTTTAGGGGCGCTTGTCAAAAA
AGATTTTGTATGGAATAACTGTGAGTTTAAGAAGGGCACATCGGTGCTGCTTGATTTATATGGA
ACGAACCACGACCCTCGTCTATGGGATCATCCCGATGAATTCCGGCCGGAACGATTTGCGGAGC
GGGAAGAAAATCTGTTTGATATGATTCCTCAAGGCGGGGGGCACGCCGAGAAAGGCCACCGCTG
TCCAGGGGAAGGCATTACAATTGAAGTCATGAAAGCGAGCCTGGATTTCCTCGTCCATCAGATT
GAATACGATGTTCCGGAACAATCACTGCATTACAGTCTCGCCAGAATGCCATCATTGCCTGAAA
GCGGCTTCGTAATGAGCGGAATCAGACGAAAAGTTAA
```

D) SEQ ID NO:4

```
MNEQIPHDKSLDNSLTLLKEGYLFIKNRTERYNSDLFQARLLGKNFICMTGAEAAKVFYDTDRF
QRQNALPKRVQKSLFGVNAIQGMDGSAHIHRKMLFLSLMTPPHQKRLAELMTEEWKAAVTRWEK
ADEVVLFEEAKEILCRVACYWAGVPLKETEVKERADDFIDMVDAFGAVGPRHWKGRRARPRAEE
WIEVMIEDARAGLLKTTSGTALHEMAFHTQEDGSQLDSRMAAIELINVLRPIVAISYFLVFSAL
ALHEHPKYKEWLRSGNSREREMFVQEVRRYYPFGPFLGALVKKDFVWNNCEFKKGTSVLLDLYG
TNHDPRLWDHPDEFRPERFAEREENLFDMIPQGGGHAEKGHRCPGEGITIEVMKASLDFLVHQI
EYDVPEQSLHYSLARMPSLPESGFVMSGIRRKS
```

FIG. 1 (continued)

E) SEQ ID NO:5: ALICYCLOBACILLUS ACIDOCALDARIUS LAA1 CTG162, WHOLE GENOME SHOTGUN SEQUENCE

ATGAATCAGTGCATTCCGCGCGATCGAACGTTTGACAGCAGCCTCGCCTTGATAAAGGAAGGGT
ATTTGTTCATCAAAAATCGAGTTGATCAATACCAATCCGACATCTTCGAAGCGCGTCTCCTCCT
GGAAAATGTGGTATGCATGCACGGAGCAGAGGCGGCAAAACTCTTCTACAATACGGAACTGTTT
CAACGCCAAGGTGCTCTTCCGAAGCGGGTTCAAAAGACGCTTTTCGGAGAAAACGCCATCCAAA
CCCTTGATGGTACAGCGCATCTTCACCGTAAGCAGCTGTTTCTGTCGTTGTTGACGCCGGATCA
AGAAAAATCCCTTGCGACGCTCGCGACAACGCAGTGGAGGGAGTGCGCGAAGGTATGGGAGAAC
GCGGATAGGGTTGTGCTATTTGAAGAGGCCAAGCGGATGTTATGTCGGATCGCATGTCAGTGGA
CCGGGGTTCCGCTGGATGAATCGGAGGTGTCAAAGCGGGCCGACGATTTTGGGGCGATGGTGGA
CGCGTTTGGAGCGGTTGGTCCGCGACATTGGAAAGGCCGGAGAGCTCGGGCCAGAGCAGAAGCA
TGGCTCCGGCAGATGATTGACGAGATACGAATCGGATTGCGTAGTGTAGATGAACATACGCCGC
TCCATGTGGTGGCCTTTTGGCGTGACGTGAATGGAAACCTCTTGGATGCTCAGATGGTTGCAAT
CGAGTTAATCAATCTGCTACGACCCATCGTAGCTATTTCTACTTTCATCACGTTTTCAGCCCTG
GCCCTGCACGAACACCCGACATGGCGAGACCGATTGAAGGCGCGCAATGAAGCGGATATCGAGA
TGTTTGTGCAAGAGGTTCGTCGCTACTATCCGTTCGCGCCATTTCTCGGTGCCAGAGTGAAAAA
GGATTTTGTGTGGAGGGGATACGAATTTAAAAGAGGGACCCTTGTGTTGCTGGATGTGTATGGA
ACCCATCATGATGCCCGCCTCTGGGATTCCCCAAATGAGTTTCGACCCGAACGATTCATGAGAA
AAACAGTTGGGCCGTTTGATTTGATTCCTCAAGGTGGAGGGGACTCTCACACCGGTCATCGTTG
CCCTGGTGAAGGCGCCACCATCGAGATTATGAAGGCGAGCGTGGATTTTCTGGTTAACCAAATT
GACTTCGAAGTGCCCGCTCAGGACCTCAGTTACAGATTGGATGTTATGCCGACGTTGCCAAAGA
GCGGATTTGTGCTGACCCATGTTCATCGGAAGTTCATAGCTTCTCCGACCATTGCTACACCTAA
TGGTTCTGAAGCTCTTCCTTCAGAAGTCTAA

F) SEQ ID NO:6

MNQCIPRDRTFDSSLALIKEGYLFIKNRVDQYQSDIFEARLLLENVVCMHGAEAAKLFYNTELF
QRQGALPKRVQKTLFGENAIQTLDGTAHLHRKQLFLSLLTPDQEKSLATLATTQWRECAKVWEN
ADRVVLFEEAKRMLCRIACQWTGVPLDESEVSKRADDFGAMVDAFGAVGPRHWKGRRARARAEA
WLRQMIDEIRIGLRSVDEHTPLHVVAFWRDVNGNLLDAQMVAIELINLLRPIVAISTFITFSAL
ALHEHPTWRDRLKARNEADIEMFVQEVRRYYPFAPFLGARVKKDFVWRGYEFKRGTLVLLDVYG
THHDARLWDSPNEFRPERFMRKTVGPFDLIPQGGGDSHTGHRCPGEGATIEIMKASVDFLVNQI
DFEVPAQDLSYRLDVMPTLPKSGFVLTHVHRKFIASPTIATPNGSEALPSEV

FIG. 1 (continued)

G) SEQ ID NO:7: STAPHYLOCOCCUS MASSILIENSIS S46 CONTIG01, WHOLE GENOME SHOTGUN SEQUENCE

ATGTTTGTAGATTCGATACTTGTGTTAAGATTAAATTTATTAAAAACGGGTATACAATTAGAAA
TGAAAAATGGGGGAATCAAAGTGGCAAAGAAACTACCTAAGGTTAAAGGCCTAGATAACACAGT
AGACATTATTAAAGGCGGGTATACATACGTACCTGGCAAATTAGAAGAATTTGATTCTAAAGCA
TTTGAAGTACGCGCATTAGGCGGTAAGAAAATTGCTGTTATGAGCGGTAAGAAGCGGCAGAAA
TTTTCTATGATAATGAAAAATGGAAAGACAAGGTACTTTACCAAAACGTATCGTAAACACTTT
ATTTGGTAAAGGTGCAATTCATACAACTGCTGGTAAGAAGCACGTTGACCGTAAAGCTTTATTT
ATGTCACTTATGACAGATGAAAATCTTAACTACTTACGTGAATTAACACGTAATTATTGGTTCA
TGAATACTGAACGTATGCAAAGCATGGATAAAGTTAACGTATATAACGAATCAATTTATATGTT
AACTAAAATCGGCTTCCGTTGGGCTGGTATCATCCAAACGCCTGAAGAAGCAGAACAAAATGCG
AAAGACATGGATACTATGATTAACTCATTCGTATCTTTAGGTTCAGCTTACAAAGGTTATAAGA
AAGCTAAAAAAGCACGTAAACGTGTTGAAGATTTCTTAGAAAAACAAATTATCGATGTGCGTAA
AGGTAAATTACACCCTGAAGAAGGTACTGCGTTATACGAATTCGCGCATTGGGAAGATTTAAAC
GATAACCCAATGGATTCTCACTTATGTGCAGTAGACTTAATGAACGTTGTGCGCCCATTAGCTG
CAATCAACCGTTTCATCAGCTATGGTGTTAAAGTATTAATCGAATTCGATCAAGAAAAAGAAAA
ATTACGTCTTGAAAATAATGAAGACTATGCGTATAAATTCGCTCAAGAAGTACGTCGTATCTTC
CCATTCGTACCATACTTACCAGGTAGAGCAGCTGTTGATTTAGAATATGACGGCTACAAAATCC
CTGCAGGTATGATGACAGCATTAGATGTTTATGGTACGACACATGATGAAGATTTATGGGAAAA
CCCAGACCAATTCAATCCTAACCGTTTTGATAACTGGGACGGTAGCCCATTCGACTTAATTCCA
CAAGGTGGCGGTGACTTCTATACGAACCACAGATGTGCTGGTGAGTGGATCACAGTTATCATTA
TGGAAGAAACAATGAAATATTTCGCGAATAAGATTGAATTTGATGTACCGTCTCAAGATTTATC
AGTTAAGCTTGATAAATTACCAGGTAACGTAACAAGCGGTACAATCATTAGTAATGTACGTCCA
CGTGTTGCGCGTAAATAA

H) SEQ ID NO:8

MFVDSILVLRLNLLKTGIQLEMKNGGIKVAKKLPKVKGLDNTVDIIKGGYTYVPGKLEEFDSKA
FEVRALGGKKIAVMSGKEAAEIFYDNEKMERQGTLPKRIVNTLFGKGAIHTTAGKKHVDRKALF
MSLMTDENLNYLRELTRNYWFMNTERMQSMDKVNVYNESIYMLTKIGFRWAGIIQTPEEAEQNA
KDMDTMINSFVSLGSAYKGYKKAKKARKRVEDFLEKQIIDVRKGKLHPEEGTALYEFAHWEDLN
DNPMDSHLCAVDLMNVVRPLAAINRFISYGVKVLIEFDQEKEKLRLENNEDYAYKFAQEVRRIF
PFVPYLPGRAAVDLEYDGYKIPAGMMTALDVYGTTHDEDLWENPDQFNPNRFDNWDGSPFDLIP
QGGGDFYTNHRCAGEWITVIIMEETMKYFANKIEFDVPSQDLSVKLDKLPGNVTSGTIISNVRP
RVARK

FIG. 1 (continued)

(A) Codon-optimized (for expression in E. coli) nucleotide sequence encoding Sm46 from Staphylococcus Massiliensis strain S46 (SEQ ID NO:9) and flanking restriction sites

CATATGTTCGTGGATAGCATTCTGGTTCTGCGCCTGAACCTGCTGAAGACAGGCATCCAGCTGG
AGATGAAGAACGGTGGCATCAAAGTGGCAAAAAAGCTGCCTAAAGTGAAAGGTCTGGACAACAC
CGTGGACATCATCAAGGGTGGCTATACCTACGTGCCTGGCAAACTGGAGGAGTTCGACAGCAAA
GCATTCGAAGTGCGCGCCCTGGGTGGCAAGAAGATCGCAGTGATGAGCGGCAAGGAAGCCGCCG
AGATTTTTTATGATAACGAAAAAATGGAGCGTCAGGGTACCCTGCCGAAGCGCATCGTGAACAC
ACTGTTCGGTAAAGGCGCCATTCATACCACCGCCGGCAAGAAACATGTGGATCGCAAGGCACTG
TTCATGAGTCTGATGACCGATGAAAATTTAAATTATCTGCGCGAACTGACACGCAACTATTGGT
TTATGAATACAGAACGCATGCAGAGCATGGATAAAGTGAATGTGTACAATGAAAGCATTTATAT
GCTGACCAAAATTGGCTTCCGCTGGGCCGGTATCATTCAGACCCCTGAAGAGGCCGAGCAGAAT
GCCAAAGACATGGACACCATGATCAACAGCTTTGTGAGCCTGGGCAGCGCCTACAAGGGTTACA
AAAAAGCCAAGAAAGCCCGCAAGCGCGTGGAAGATTTTCTGGAGAAACAAATTATCGACGTTCG
TAAAGGCAAACTGCATCCGGAGGAAGGTACCGCCCTGTACGAATTCGCCCATTGGGAAGACCTG
AACGATAACCCGATGGACAGCCATCTGTGCGCCGTTGATCTGATGAACGTTGTTCGCCCGCTGG
CAGCAATTAACCGCTTCATTAGCTACGGCGTTAAAGTGCTGATCGAATTCGACCAGGAAAAAGA
AAAGCTGCGCCTGGAGAACAACGAGGACTACGCCTACAAGTTCGCACAGGAAGTGCGCCGTATC
TTTCCGTTCGTGCCTTACTTACCGGGTCGCGCCGCCGTGGATCTGGAGTATGATGGCTATAAGA
TCCCGGCCGGTATGATGACCGCCCTGGATGTTTACGGTACCACACACGATGAGGATCTGTGGGA
GAATCCGGATCAGTTCAACCCGAATCGTTTTGATAACTGGGACGGCAGTCCGTTTGATCTGATT
CCGCAGGGCGGTGGCGATTTCTACACCAATCATCGTTGCGCCGGCGAGTGGATCACCGTGATTA
TTATGGAAGAAACAATGAAATACTTTGCCAACAAAATTGAATTCGATGTGCCGAGTCAGGACCT
GAGCGTTAAACTGGACAAACTGCCTGGCAACGTGACCAGCGGTACCATCATTAGCAACGTGCGT
CCGCGTGTTGCCCGCAAATAACTCGAG

(B) SEQ ID NO: 13

AKKLPKVKGLDNTVDIIKGGYTYVPGKLEEFDSKAFEVRALGGKKIAVMSGKEAAEIFYDNEKM
ERQGTLPKRIVNTLFGKGAIHTTAGKKHVDRKALFMSLMTDENLNYLRELTRNYWFMNTERMQS
MDKVNVYNESIYMLTKIGFRWAGIIQTPEEAEQNAKDMDTMINSFVSLGSAYKGYKKAKKARKR
VEDFLEKQIIDVRKGKLHPEEGTALYEFAHWEDLNDNPMDSHLCAVDLMNVVRPLAAINRFISY
GVKVLIEFDQEKEKLRLENNEDYAYKFAQEVRRIFPFVPYLPGRAAVDLEYDGYKIPAGMMTAL
DVYGTTHDEDLWENPDQFNPNRFDNWDGSPFDLIPQGGGDFYTNHRCAGEWITVIIMEETMKYF
ANKIEFDVPSQDLSVKLDKLPGNVTSGTIISNVRPRVARK

FIG. 5

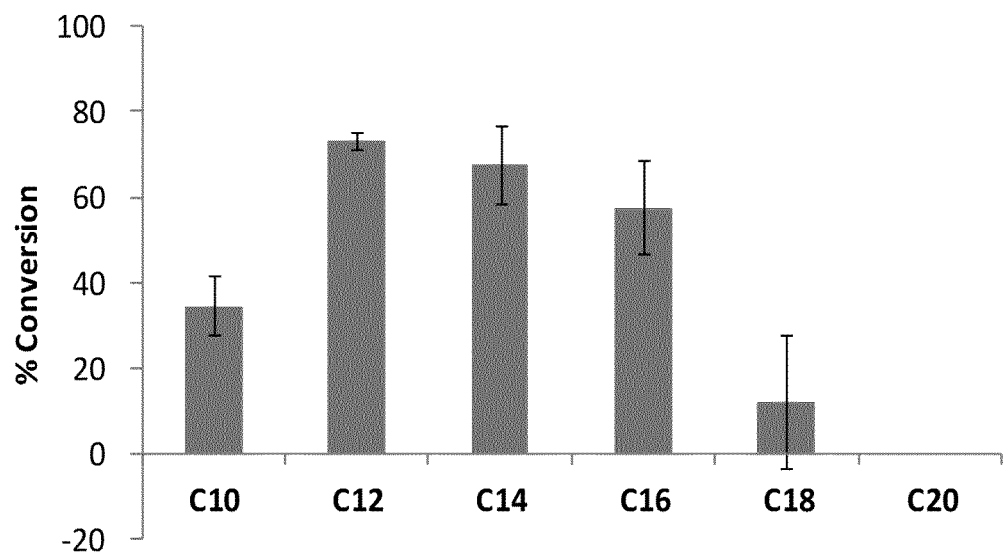
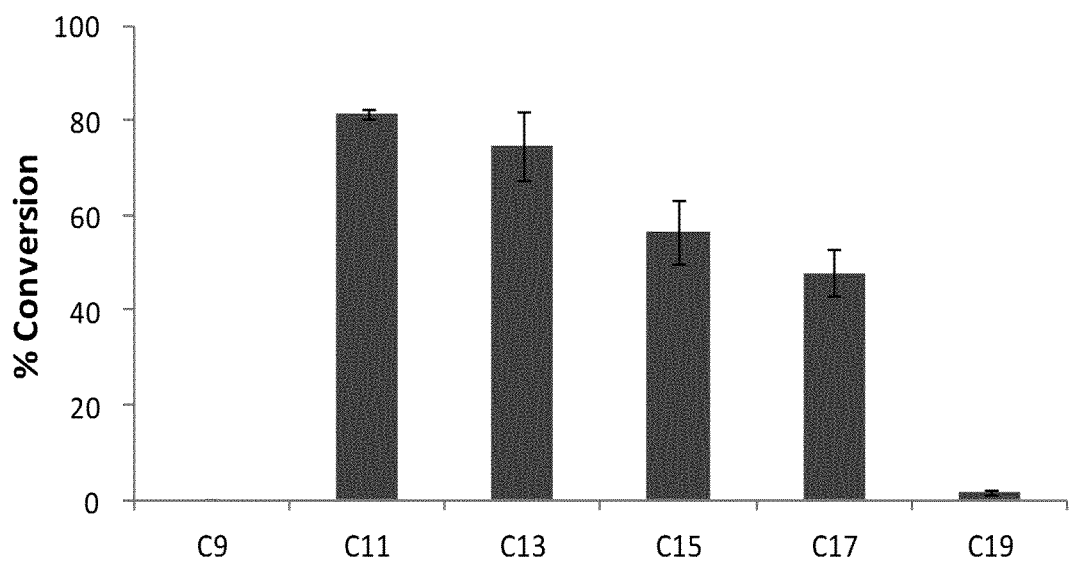
FIG. 6

1

PRODUCTION OF ALPHA-OLEFINS

CROSS-REFERENCE TO RELATED APPLICATIONS

This application is a U.S. national stage entry under 35 U.S.C. § 371 of PCT International Patent Application No. PCT/EP2016/065389, filed Jun. 30, 2016, which claims priority to European Patent Application No. 15174554.4, filed Jun. 30, 2015, the contents of which are incorporated herein by reference in their entirety.

TECHNICAL FIELD

The application generally relates to biosynthetic processes. In particular, the application relates to the biosynthesis of α-olefins.

BACKGROUND

Unsaturated hydrocarbons such as α-olefins are an industrially important group of molecules which can serve as precursors for lubricants and surfactants in addition to being used in fuels, or as feedstock for further chemical conversion to e.g. fuels, polymers, plastics, textiles, solvents, adhesives, etc.

α-Olefins, more particularly linear α-olefins, have traditionally been produced from petroleum sources through oligomerization of ethylene but it would be advantageous to find alternative methods for producing such α-olefins, notably from renewable resources. Moreover, the chemical synthesis results in a mixture of linear α-olefins which exhibit different carbon chain length. Such mixture may not be desired as feedstock for further chemical conversion such as the production of poly-α-olefins of interest.

Microbial production of olefins has been reported. Examples include a three-gene cluster responsible for generating alkenes with internal double bonds through the head-to-head condensation of two fatty acyl-coenzyme A (acyl-CoA) molecules in *Micrococcus luteus* (Beller et al. 2010 Appl Environ Microbiol 76:1212-1223); a unique P450 decarboxylase OleT$_{JE}$ from *Jeotgalicoccus* sp. ATCC 8456, which directly decarboxylates $C_{12}$ to $C_{20}$ free fatty acids to form α-olefins in presence of $H_2O_2$ (WO 2009/085278, Rude et al. 2011 Appl Environ Microbiol 77:1718-1727, Liu et al. 2014 Biotechnology for Biofuels 7:28); another enzyme of the cyp152 P450 enzyme family, namely P450$_{BSβ}$ from *Bacillus subtilis* subsp. *subtilis* str. 168, for which decarboxylase activity on palmitic acid has been shown (WO 2009/085278, Rude et al. 2011); and a type I polyketide synthase from *Synechococcus* sp. PCC 7002, which is capable of transforming fatty acyl-ACPs into α-olefins via sequential polyketide synthase chain elongation, keto reduction, sulfonation mediated by its sulfotransferase domain, and the coupled hydrolysis and decarboxylation catalyzed by the thioesterase domain (Mendez-Perez et al. 2011 Appl Environ Microbiol 77:4264-4267).

In general, there is a need for alternative production methods of α-olefins, and more particularly improved processes that allow production of α-olefins at a lower cost and/or that are more environmental friendly. It is also desired to provide production methods which allow tailoring of the carbon chain length of the α-olefins, more particularly a production method for medium-chain α-olefins (i.e. α-olefins having a carbon chain length comprised between 7 and 13), more particularly for $C_{11}$ α-olefins.

SUMMARY OF THE INVENTION

The present invention solves one or more of the above described problems of the prior art. In particular, methods are provided for the production of α-olefins which allow controlling the carbon chain length of the α-olefins.

The present invention is based, at least in part, on the discovery that certain genomic sequences of *Alicyclobacillus acidocaldarius* and *Staphylococcus massiliensis* encode enzymes having free fatty acid decarboxylase activity. None of these organisms have previously been reported to produce terminal olefins. It has further been found that certain polypeptides can be identified which have specific decarboxylase activity on medium-chain free fatty acids, in particular $C_8$ to $C_{12}$ free fatty acids, more particularly on $C_{12}$ free fatty acids, thereby producing medium-chain α-olefins, in particular $C_7$ to $C_{11}$ α-olefins, more particularly $C_{11}$ α-olefins. The application provides examples thereof, more particularly an olefin-producing enzyme (Sm46) identified in *Staphilococcus massiliensis*, the P450$_{BSβ}$ fatty acid hydroxylase (Bs168) from *Bacillus subtilis* subsp. *subtilis* str. 168 and the decarboxylase enzyme identified in *Alicyclobacillus acidocaldarius*, have specific decarboxylase activity on $C_{12}$ free fatty acids, thereby producing $C_{11}$ α-olefins. The identification of these enzymes facilitates the further identification of similar enzymes from other organisms.

The present invention is in particular captured by any one or any combination of one or more of the below numbered aspects and embodiments (i) to (xvii) wherein:

(i) A method for the production of $C_7$-$C_{11}$ α-olefins comprising culturing a recombinant host cell comprising a recombinant nucleic acid encoding a decarboxylase enzyme under conditions suitable for the production of $C_7$ to $C_{11}$ α-olefins by said host cell, wherein the preferred substrate of said decarboxylase enzyme is an $C_8$-$C_{12}$ free fatty acid.

(ii) The method according to (i), wherein said nucleic acid encoding a decarboxylase enzyme comprises a nucleotide sequence having at least about 75%, preferably at least about 80%, more preferably at least about 95%, sequence identity to SEQ ID NO:10, SEQ ID NO:7, SEQ ID NO: 3 or SEQ ID NO: 5 and wherein said recombinant nucleic acid ensures expression or overexpression of said decarboxylase.

(iii) The method according to (i) or (ii), wherein said nucleic acid encodes a polypeptide comprising an amino acid sequence having at least 80%, preferably at least 90% identity, to SEQ ID NO:13, SEQ ID NO: 8, SEQ ID NO: 4 or SEQ ID NO: 6 or an active fragment of said polypeptide.

(iv) The method according to any one of (i) to (iii), wherein said nucleic acid encodes a polypeptide comprising the amino acid sequence of SEQ ID NO:13.

(v) The method according to any one of (i) to (iv), wherein $C_{12}$ free fatty acids are the preferred substrate of said decarboxylase, and wherein said α-olefins are $C_{11}$ α-olefins.

(vi) The method according to any one of (i) to (v), wherein said host cell is cultivated in a medium comprising $C_8$-$C_{12}$ free fatty acids, preferably $C_{12}$ free fatty acids.

(vii) The method according to any one of (i) to (vi), wherein the host cell has further been genetically engineered to produce or overproduce $C_8$-$C_{12}$ free fatty acids, preferably $C_{12}$ free fatty acids.

(viii) The method according to (vii), wherein the host cell comprises a recombinant nucleic acid encoding an enzyme involved in the production of free fatty acids with a carbon chain length comprised between 8 and 12, more particularly a $C_{12}$ free fatty acid.

(ix) The method according to (viii), wherein the host cell comprises a recombinant nucleic acid encoding a thioesterase having activity on $C_8$ to $C_{12}$ acyl-ACP, preferably on $C_{12}$ acyl-ACP.
(x) The method according to any one of (i) to (ix), wherein the host cell is an oleaginous host cell.
(xi) The method according to any one of (i) to (x), wherein the host cell is selected from the group comprising bacteria, yeasts, fungi, plants and algae.
(xii) The method according to any one of (i) to (xi), further comprising the step of recovering the α-olefins from the host cell or the culture medium.
(xiii) A method for the production of poly-α-olefins comprising the following steps:
  i) producing $C_7$-$C_{11}$ α-olefins according to a method according to any one of (i) to (xii); and
  ii) performing an oligomerization reaction using the α-olefins obtained in step i) as monomer to produce an oligomer; and optionally,
  iii) hydrogenating the oligomer produced in step ii).
(xiv) The method according to (xiii), wherein the poly-α-olefins are $C_{33}$ poly-α-olefins, wherein step i) comprises the production of $C_{11}$ α-olefins, and wherein the oligomerization reaction in step ii) is a trimerization reaction.
(xv) A composition comprising poly-α-olefins obtainable by the method according to (xiv), wherein at least 85%, preferably at least 90%, more preferably at least 95%, of the poly-α-olefins are $C_{33}$ poly-α-olefins.
(xvi) A polypeptide having decarboxylase activity, wherein said polypeptide comprises an amino acid sequence having at least 80%, preferably at least 90%, identity to SEQ ID NO:13.
(xvii) An isolated nucleic acid encoding an enzyme having decarboxylase activity, wherein said nucleic acid comprises a nucleotide sequence having at least about 80%, more preferably at least about 95%, sequence identity to SEQ ID NO: 7 or SEQ ID NO: 5.
(xviii) The polypeptide according to (xvi) or the isolated nucleic acid according to (xvii), wherein $C_8$ to $C_{14}$ free fatty acids, preferably $C_8$ to $C_{12}$ free fatty acids, more preferably $C_{12}$ free fatty acids are the preferred substrate of said decarboxylase.
(xix) The isolated nucleic acid according to (xvii) or (xviii), wherein said nucleic acid comprises a nucleotide sequence having at least about 95% sequence identity to SEQ ID NO: 7.
(xx) A vector comprising at least one regulatory sequence operatively coupled to the nucleic acid sequence of any of (xvii) to (xix).
(xxi) A host cell comprising the nucleic acid according to any of (xvii) to (xix) integrated into its genome or the vector according to (xx).
(xxii) The host cell of (xxi), which is an oleaginous eukaryotic microalgae or oleaginous yeast.
(xxiii) Use of a host cell according to (xxi) or (xxii) for the industrial production of lubricants.
(xxiv) Lubricant comprising poly-α-olefins obtainable by a method according to (xiii) or (xiv).
(xxv) Lubricant according to (xxiv), wherein said poly-α-olefins are biosourced poly-α-olefins.
(xxvi) Lubricant according to (xxiv) or (xxv), wherein at least 50%, preferably at least 85%, of said poly-α-olefins consist of $C_{33}$ poly-α-olefins.
(xxvii) Lubricant according to any one of (xxiv) to (xxvi), wherein said lubricant is an automotive lubricant.

BRIEF DESCRIPTION OF THE FIGURES

The teaching of the application is illustrated by the following Figures which are to be considered as illustrative only and do not in any way limit the scope of the claims.
FIG. 1: Nucleotide (A,C,E,G) and amino acid (B,D,F,H) sequences of $OleT_{JE}$ (A,B), Bs168 (C,D), Aa162 (E,F) and Sm46 (G,H).
FIG. 2: Plasmid map of pET28a.
FIG. 5: (A) Codon-optimized (for expression in E. coli) nucleotide sequences encoding Sm46 and a truncated variant Sm46-del29 that has the N-terminal 29 amino acids deleted (SEQ ID NO:9 and SEQ ID NO:10, respectively) with flanking restriction sites. Codon-optimized (for expression in E. coli) nucleotide sequence (SEQ ID NO: 9) encoding Sm46 is shown; Nde I and Xho I restriction sites are indicated in bold, the deleted sequence to encode for the truncated variant Sm46-del29 is underlined. (B) Amino acid sequence of Sm46-del29 (SEQ ID NO:13).
FIG. 6: In vitro conversion of free fatty acids into α-olefins by a truncated variant of Sm46: Sm46-del29. Conversion percentages of the free fatty acid substrates (A) and the corresponding α-alkene products (B) are shown.

DETAILED DESCRIPTION OF THE INVENTION

Figure 2:
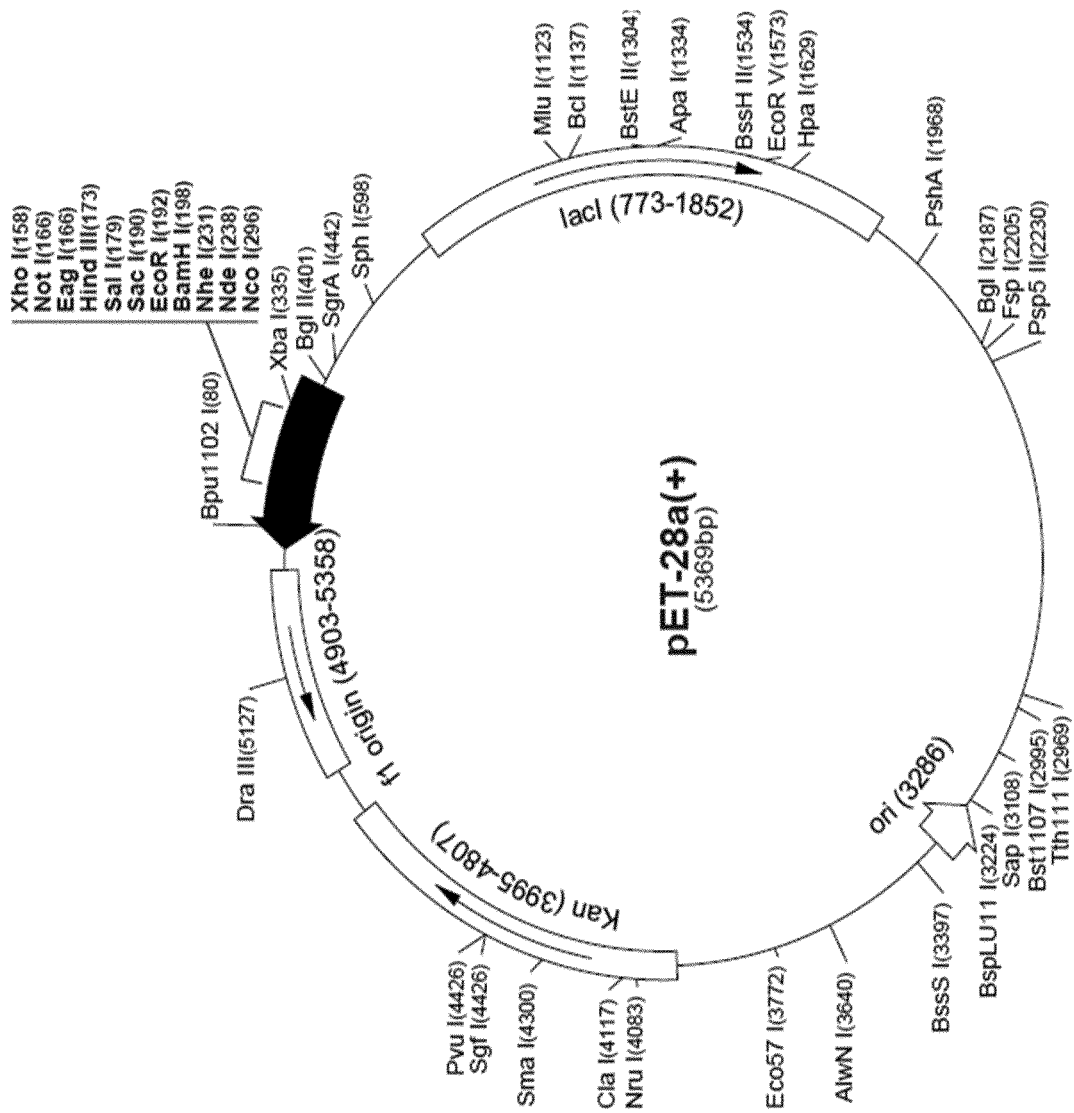

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.
As used herein, the singular forms "a", "an", and "the" include both singular and plural referents unless the context clearly dictates otherwise.
The terms "comprising", "comprises" and "comprised of" as used herein are synonymous with "including", "includes" or "containing", "contains", and are inclusive or open-ended and do not exclude additional, non-recited members, elements or method steps. Where reference is made to embodiments as comprising certain elements or steps, this encompasses also embodiments which consist essentially of the recited elements or steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Standard reference work setting forth the general principles of biochemistry includes Biochemical Pathways: An Atlas of Biochemistry and Molecular Biology, ed. Michal, G, John Wiley and Sons, Inc., New York, US, 1999.

The term "olefin" or "alkene" refers herein to molecules composed of carbon and hydrogen, containing at least one carbon-carbon double bond. Olefins containing one carbon-carbon double bond are denoted herein as mono-unsaturated hydrocarbons and have the chemical formula $C_nH_{2n}$, where n equals at least two.

"Alpha-olefins", "α-olefins", "1-alkenes" or "terminal olefins" are used as synonyms herein and denote olefins or alkenes having a double bond at the primary or alpha (α) position. "Linear α-olefins" or "LAO" as used herein refer to α-olefins that have a linear hydrocarbon chain, whereas "branched α-olefins" have a branch on one or more carbon atoms of the hydrocarbon chain. The term "medium-chain α-olefins" is used herein to denote α-olefins with 7 to 13 carbons and encompasses any one or more of $C_7$ α-olefins, $C_8$ α-olefins, $C_9$ α-olefins, $C_{10}$ α-olefins, $C_{11}$ α-olefins, $C_{12}$ α-olefins, and $C_{13}$ α-olefins. The term "uneven-numbered α-olefins" refers to α-olefins wherein the number of carbon atoms is not even in number. Thus, uneven-numbered medium-chain α-olefins encompass $C_7$, $C_9$, $C_{11}$ and $C_{13}$ α-olefins.

As used herein, the term "fatty acid" or "free fatty acid" means a carboxylic acid having the formula RCOOH, or a salt (RCOO—) thereof. R represents an aliphatic group, preferably an alkyl group. Fatty acids can be saturated, mono-unsaturated, or poly-unsaturated. The term "medium-chain fatty acid" or "medium-chain free fatty acid" as used herein denotes a fatty acid or free fatty acid having 8 to 14 carbon atoms. The term "even-numbered fatty acids" refers to fatty acids wherein the number of carbon atoms is even in number. Thus, even-numbered medium-chain fatty acids encompass $C_8$, $C_{10}$, $C_{12}$ and $C_{14}$ fatty acids.

As used herein, the term "host cell" refers to a cell that can be used to produce an α-olefin as described herein. A host cell may be an isolated cell or a cell line grown in culture, or a cell which resides in a living tissue or organism.

As used herein, the terms "microbial", "microbial organism" or "micro-organism" are intended to mean any organism that exists as a microscopic cell that is included within the domains of archaea, bacteria or eukaryotes. Therefore, the term is intended to encompass prokaryotic or eukaryotic cells or organisms having a microscopic size and includes bacteria, archaea and eubacteria such as cyanobacteria of all species as well as eukaryotic micro-organisms such as fungi, including yeasts, and algae. The term also includes cell cultures of any species that can be cultured for the production of a biochemical.

The term "oleaginous" as used herein with reference to a host cell denotes cells characterized by their lipid accumulation capability. Typically, their biomass contains over 20% lipids in dry matter.

The "algae" group encompasses, without limitation, (i) several eukaryotic phyla, including the Rhodophyta (red algae), Chlorophyta (green algae), Dinoflagellata, Haptophyta, (ii) several classes from the eukaryotic phylum Heterokontophyta which include without limitation the classes Bacillariophycea (diatoms), Eustigmatophycea, Phaeophyceae (brown algae), Xanthophyceae (yellow-green algae) and Chrysophyceae (golden algae), and (iii) the prokaryotic phylum Cyanobacteria (blue-green algae).

The term "algae" includes for example genera selected from: *Achnanthes, Amphora, Anabaena, Anikstrodesmis, Arachnoidiscusm, Aster, Botryococcus, Chaetoceros, Chlamydomonas, Chlorella, Chlorococcum, Chorethron, Cocconeis, Coscinodiscus, Cyclotella, Cylindrotheca, Dunaliella, Emiliana, Euglena, Fistulifera, Fragilariopsis, Gyrosigma, Hematococcus, Isochrysis, Lampriscus, Monochrysis, Monoraphidium, Nannochloris, Nannnochloropsis, Navicula, Neochloris, Nephrochloris, Nephroselmis, Nitzschia, Nodularia, Nostoc, Odontella, Oochromonas, Oocystis, Oscillartoria, Pavlova, Phaeodactylum, Playtmonas, Pleurochrysis, Porhyra, Pseudoanabaena, Pyramimonas, Stichococcus, Synechococcus, Synechocystis, Tetraselmis, Thalassiosira*, and *Trichodesmium*.

The terms "genetically engineered" or "genetically modified" or "recombinant" as used herein with reference to a host cell denote a non-naturally occurring host cell, as well as its recombinant progeny, that has at least one genetic alteration not found in a naturally occurring strain of the referenced species, including wild-type strains of the referenced species. Such genetic modification is typically achieved by technical means (i.e. non-naturally) through human intervention and may include, e.g., the introduction of an exogenous nucleic acid and/or the modification, overexpression, or deletion of an endogenous nucleic acid.

The term "exogenous" or "foreign" as used herein is intended to mean that the referenced molecule, in particular nucleic acid, is not naturally present in the host cell.

The term "endogenous" or "native" as used herein denotes that the referenced molecule, in particular nucleic acid, is present in the host cell.

By "recombinant nucleic acid" when referring to a nucleic acid in a recombinant host cell, is meant that at least part of said nucleic acid is not naturally present in the host cell in the same genomic location. For instance a recombinant nucleic acid can comprise a coding sequence naturally occurring in the host cell under control of an exogenous promoter, or it can be an additional copy of a gene naturally occurring in the host cell, or a recombinant nucleic acid can comprise an exogenous coding sequence under the control of an endogenous promoter.

By "nucleic acid" is meant oligomers and polymers of any length composed essentially of nucleotides, e.g., deoxyribonucleotides and/or ribonucleotides. Nucleic acids can comprise purine and/or pyrimidine bases and/or other natural (e.g., xanthine, inosine, hypoxanthine), chemically or biochemically modified (e.g., methylated), non-natural, or derivatised nucleotide bases. The backbone of nucleic acids can comprise sugars and phosphate groups, as can typically be found in RNA or DNA, and/or one or more modified or substituted sugars and/or one or more modified or substituted phosphate groups. Modifications of phosphate groups or sugars may be introduced to improve stability, resistance to enzymatic degradation, or some other useful property. A "nucleic acid" can be for example double-stranded, partly double stranded, or single-stranded. Where single-stranded, the nucleic acid can be the sense strand or the antisense strand. The "nucleic acid" can be circular or linear. The term "nucleic acid" as used herein preferably encompasses DNA and RNA, specifically including genomic, hnRNA, pre-mRNA, mRNA, cDNA, recombinant or synthetic nucleic acids, including vectors.

By "encoding" is meant that a nucleic acid sequence or part(s) thereof corresponds, by virtue of the genetic code of an organism in question, to a particular amino acid sequence, e.g., the amino acid sequence of a desired polypeptide or protein. By means of example, nucleic acids "encoding" a particular polypeptide or protein, e.g. an enzyme, may encompass genomic, hnRNA, pre-mRNA, mRNA, cDNA, recombinant or synthetic nucleic acids.

Preferably, a nucleic acid encoding a particular polypeptide or protein may comprise an open reading frame (ORF) encoding said polypeptide or protein. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a polypeptide or protein. Hence, the term may be synonymous with "coding sequence" as used in the art.

The nucleic acids taught herein may encode more than one polypeptide or protein. Such nucleic acids are denoted as "polycistronic" nucleic acids and typically comprise several ORFs or coding sequences, each encoding a polypeptide or protein.

The terms "polypeptide" and "protein" are used interchangeably herein and generally refer to a polymer of amino acid residues linked by peptide bonds, and are not limited to a minimum length of the product. Thus, peptides, oligopeptides, polypeptides, dimers (hetero- and homo-), multimers (hetero- and homo-), and the like, are included within the definition. Both full-length proteins and fragments thereof are encompassed by the definition. The terms also include post-expression modifications of the polypeptide, for example, glycosylation, acetylation, phosphorylation, etc. Furthermore, for purposes of the present invention, the terms also refer to such when including modifications, such as deletions, additions and substitutions (e.g., conservative in nature), to the sequence of a native protein or polypeptide.

The term "enzyme" as used herein denotes a biological molecule that catalyzes a chemical reaction. The term encompasses single enzymes, i.e. single catalytic entities, as well as systems comprising more than one catalytic entity. The enzymes described herein can naturally possess the recited activity or they can be engineered to exhibit said activity.

As used herein, "fatty acid enzyme" means any enzyme involved in fatty acid biosynthesis. As used herein, the term "fatty acid biosynthetic pathway" means a biosynthetic pathway that produces fatty acids. Fatty acid enzymes can be expressed or over-expressed in a host cell to produce fatty acids.

As used herein, the terms "purify," "purified," or "purification" means the removal or isolation of a molecule from its environment by, for example, isolation or separation. As used herein, these terms also refer to the removal of contaminants from a sample. For example, when α-olefins are produced in a host cell, the olefins can be purified by the removal of other cellular components (e.g., nucleic acids, polypeptides, lipids, carbohydrates, or other hydrocarbons).

The terms "purify," "purified," and "purification" do not require absolute purity. They are relative terms.

As used herein, the terms "identity" and "identical" and the like refer to the sequence similarity between two polymeric molecules, e.g., between two nucleic acid molecules or polypeptides. Methods for comparing sequences and determining sequence identity are well known in the art. By means of example, percentage of sequence identity refers to a percentage of identical nucleic acids or amino acids between two sequences after alignment of these sequences. Alignments and percentages of identity can be performed and calculated with various different programs and algorithms known in the art. Preferred alignment algorithms include BLAST (Altschul, 1990; available for instance at the NCBI website) and Clustal (reviewed in Chenna, 2003; available for instance at the EBI website). Preferably, BLAST is used to calculate the percentage of identity between two sequences, such as the "Blast 2 sequences" algorithm described by Tatusova and Madden 1999 (FEMS Microbiol Lett 174: 247-250), for example using the published default settings or other suitable settings (such as, e.g., for the BLASTN algorithm: cost to open a gap=5, cost to extend a gap=2, penalty for a mismatch=−2, reward for a match=1, gap x_dropoff=50, expectation value=10.0, word size=28; or for the BLASTP algorithm: matrix=Blosum62, cost to open a gap=11, cost to extend a gap=1, expectation value=10.0, word size=3).

The term "renewable" is used herein to refer to a material (e.g. a molecule, a composition or a product) that can be produced or is derivable from a natural resource which is periodically (e.g., annually or perennially) replenished through the actions of plants of terrestrial, aquatic or oceanic ecosystems (e.g., agricultural crops, edible and non-edible grasses, forest products, seaweed, or algae), or microorganisms (e.g., bacteria, fungi, or yeast).

The term "renewable resource" refers to a natural resource that can be replenished within a 100 year time frame. The resource may be replenished naturally, or via agricultural techniques. Renewable resources include, for example but without limitation, plants, animals, fish, bacteria, fungi, yeasts, algae and forestry products. They may be naturally occurring, hybrids, or genetically engineered organisms. Natural resources such as crude oil, coal, and peat which take longer than 100 years to form are not considered to be renewable resources.

The term "bio-based content" refers herein to the amount of carbon from a renewable resource in a material as a percentage of the mass of the total organic carbon in the material, as determined by standard ASTM D6866.

The term "biosourced" with respect to a material (e.g. a molecule, a composition or a product) means that such material is derived from starting materials of renewable origin (i.e. from renewable resources). Accordingly, subject to typical measurement errors, a biosourced material has a bio-based content of at least 90%, preferably at least 95%, more preferably at least about 96%, 97% or 98%, even more preferably at least about 99% such as about 100%.

The present application generally relates to the biosynthesis of olefins, in particular α-olefins, more particularly medium-chain α-olefins.

More particularly, the application provides nucleotide sequences encoding medium-chain free fatty acid decarboxylases and the polypeptides encoded thereby, recombinant organisms comprising said nucleotide sequences, methods of production of medium-chain α-olefins using said polypeptides or said recombinant organisms and products obtained by these methods.

Nucleotide Sequences

The application provides nucleic acids encoding enzymes having decarboxylase activity on medium-chain free fatty acids, which are of interest for the production of the corresponding medium-chain α-olefins. Indeed, the inventors have identified a number of nucleic acid sequences which encode enzymes having decarboxylase activity on medium-chain free fatty acids. In particular embodiments these nucleic acids encode decarboxylase enzymes for which medium-chain free fatty acids are preferred substrates.

Nucleotide sequences encoding enzymes having medium-chain free fatty acid decarboxylase activity, in particular $C_8$-$C_{12}$ free fatty acid decarboxylase activity, more particularly $C_{12}$ free fatty acid decarboxylase activity, and accordingly suitable for use in the methods envisaged herein include the sequence encoding the P450$_{BSβ}$ fatty acid hydroxylase (Bs168) from *Bacillus subtilis* subsp. *subtilis* str. 168 (SEQ ID NO:3); a genomic sequence of *Alicyclobacillus acidocaldarius* encoding an olefin-producing enzyme (Aa162) (SEQ ID NO:5); and a genomic sequence of *Staphylococcus massiliensis* encoding an olefin-producing enzyme (Sm46) (SEQ ID NO:7), as well as variants of these sequences. Variant nucleotide sequences may for instance be codon-optimized sequences for recombinant expression in a host cell of choice. For instance, nucleotide sequences having at least about 70% or 75%, preferably at least about 80%, more preferably at least about 85%, 90% or 95%, even more preferably at least about 96%, 97%, 98% or 99% sequence identity to SEQ ID NO:3, SEQ ID NO:5 or SEQ ID NO:7 and encoding enzymes having medium-chain free fatty acid decarboxylase activity, in particular $C_8$-$C_{12}$ free fatty acid decarboxylase activity, more particularly $C_{12}$ free fatty acid decarboxylase activity, are envisaged for use in the methods disclosed herein. An exemplary variant nucleotide sequence of SEQ ID NO:7 is SEQ ID NO:9, which has been codon-optimized for recombinant expression in *E. coli*.

In particular embodiments, the decarboxylase enzymes encoded by the nucleic acid sequences envisaged herein have substrate preference for medium-chain free fatty acids, preferably $C_8$-$C_{12}$ free fatty acids, more preferably $C_{12}$ free fatty acids.

The inventors are the first to identify the nucleic acid sequence of *Alicyclobacillus acidocaldarius* (SEQ ID NO:5) and a genomic sequence of *Staphylococcus massiliensis* (SEQ ID NO:7) encoding olefin-producing enzymes (termed Aa162 and Sm46, respectively). More particularly, the nucleic acid sequence of *Alicyclobacillus acidocaldarius* (SEQ ID NO:5) was found to encode a decarboxylase (Aa162, SEQ ID NO:6) acting preferably on medium-chain free fatty acids, more particularly on $C_{12}$ free fatty acids, which can ensure an increased efficiency of the production of medium-chain α-olefins, more particularly $C_{11}$ α-olefins, and/or increased purity of said α-olefins. The genomic sequence of *Staphylococcus massiliensis* (SEQ ID NO:7) was found to encode an olefin-producing enzyme (Sm46, SEQ ID NO:8) that has decarboxylase activity on medium-chain free fatty acids. In particular, it was shown that Sm46 shows substrate preference for $C_8$-$C_{12}$ free fatty acids, more particularly $C_{12}$ free fatty acid was found to be the preferred substrate for Sm46. Also advantageously, the Sm46 polypeptide shows specific decarboxylase activity, i.e. the formation of co-products, in particular hydroxy fatty acids such as α- and β-hydroxy fatty acids, when converting free fatty acid substrate is minimal with said polypeptide.

These novel sequences allow the production of medium-chain α-olefins, in particular $C_7$-$C_{11}$ α-olefins, from the corresponding fatty acid substrates such as the production of $C_{11}$ α-olefins from $C_{12}$ free fatty acids. In addition, these sequences can be used to further identify sequences encoding enzymes having medium-chain free fatty acid decarboxylase activity, including decarboxylases for which $C_{12}$ free fatty acids are the preferred substrate.

Variants (or mutants) of sequences identified herein can be naturally occurring or they can be man-made e.g. using genetic engineering techniques. Such techniques are well known in the art and include, for example but without limitation, site directed mutagenesis, random chemical mutagenesis, and standard cloning techniques. Other exemplary techniques for mutagenesis are recombination techniques such as DNA shuffling that use fragments of existing sequences and mix them in novel combinations.

Particularly envisaged herein are variant nucleotide sequences obtained by screening a shuffling library between the nucleotide sequences set forth in SEQ ID NO:1 and SEQ ID NO:7, and a shuffling library between the nucleotide sequences set forth in SEQ ID NO:3 and SEQ ID NO:5 for recombinant nucleotide sequences encoding recombinant polypeptides having a desired biological activity, in particular decarboxylase activity, more particularly (specific) medium-chain free fatty acid decarboxylase activity such as $C_8$-$C_{12}$ free fatty acid decarboxylase activity, even more preferably the preferred substrate of these decarboxylases is a $C_8$-$C_{12}$ free fatty acid. The technique of DNA shuffling is well known in the art. Reference can be made to Stemmer (1994. Nature 370:389-391) for an exemplary shuffling technique.

The nucleotide sequences envisaged herein encoding enzymes having medium-chain free fatty acid decarboxylase activity are of particular interest for the recombinant production of medium-chain α-olefins, e.g. through the (over) expression of said nucleic acid sequences in a recombinant host cell, as detailed below.

Recombinant Host Cells

The application provides genetically engineered host cells capable of producing medium-chain α-olefins, wherein said host cells are characterized in that they comprise a recombinant nucleic acid encoding an enzyme having decarboxylase activity on $C_8$ to $C_{14}$ free fatty acids, preferably on $C_{12}$ free fatty acids as described hereinabove. For instance, these recombinant host cells may comprise an exogenous nucleic acid encoding a medium-chain free fatty acid decarboxylase, or they may over-express an endogenous nucleic acid encoding a medium-chain free fatty acid decarboxylase. In particular embodiments, the recombinant host cells comprise a recombinant nucleic acid comprising a nucleotide sequence having at least about 70% or 75%, preferably at least about 80%, more preferably at least about 85%, 90% or 95%, even more preferably at least about 96%, 97%, 98% or 99% sequence identity to SEQ ID NO: 3, SEQ ID NO: 5, SEQ ID NO: 7, SEQ ID NO:9 or SEQ ID NO:10 and encoding an enzyme having decarboxylase activity on free fatty acids with a carbon chain length comprised between 8 and 14, preferably on $C_8$-$C_{12}$ free fatty acids, more preferably on $C_{12}$ free fatty acids. In particular embodiments, the recombinant host cells comprise a recombinant nucleic acid comprising a nucleotide sequence having at least about 70% or 75%, preferably at least about 80%, more preferably at least about 85%, 90% or 95%, even more preferably at least about 96%, 97%, 98% or 99% sequence identity to SEQ ID NO:7, SEQ ID NO:9, SEQ ID NO:10, SEQ ID NO: 3, or SEQ ID NO: 5 and encoding a decarboxylase with preferred activity on $C_8$-$C_{14}$ free fatty acids, preferably on $C_8$-$C_{12}$ free fatty acids, more preferably on $C_{12}$ free fatty acids. In particular embodiments, the recombinant host cells comprise a recombinant nucleic acid comprising a nucleotide sequence that encodes a polypeptide comprising an amino acid sequence of SEQ ID NO:8, SEQ ID NO:13, SEQ ID NO:4 or SEQ ID NO:6 or a functional variant, in particular a functional fragment, of said polypeptide.

The genetically engineered host cells disclosed herein may be further genetically modified through expression of one or more recombinant nucleic acids encoding an enzyme involved in a fatty acid biosynthetic pathway. For example, the recombinant host cells may be further modified to overexpress a nucleic acid encoding an enzyme involved in an endogenous fatty acid biosynthetic pathway, or they may be further modified by introduction into the host cell of an exogenous nucleic acid encoding an enzyme involved in fatty acid synthesis. When expressed, the recombinant nucleic acid encoding the enzyme involved in fatty acid synthesis confers to the host cell the ability to produce or overproduce a fatty acid.

Each step within a fatty acid biosynthetic pathway can be modified to produce or overproduce a fatty acid of interest. For example, known genes involved in the synthesis of fatty acids can be expressed or overexpressed in a host cell to produce a desired free fatty acid, or attenuated to inhibit production of a non-desired fatty acid.

For instance, production of hydrocarbons starting from acyl-ACP is ensured by thioesterases, whereafter the production of terminal olefins is catalyzed by a decarboxylase. Accordingly, exemplary genes involved in fatty acid synthesis include genes encoding thioesterase.

In a preferred embodiment, the host cells are further genetically engineered to express or overexpress a thioesterase to induce or increase free fatty acid production. The chain length of a fatty acid substrate is controlled by thioesterase, and hence, by (over)expressing a suitable thioesterase, a free fatty acid with desired carbon chain length can be obtained. Non-limiting examples of thioesterases are provided in Table 1. Preferably, medium-chain fatty acid (MCFA)-specific thioesterases are used for (over)expression in the recombinant host cells according to the invention.

TABLE 1

Thioesterases

| GenBank accession number (UniProtKB/ Swiss-Prot) | Source organism | Gene | Preferential product produced |
|---|---|---|---|
| AAC73596 | E. coli | tesA without leader sequence | $C_{18:1}$ |
| AAC73555 | E. coli | tesB | |
| AAA34215 (Q41635); AAC49001 | Umbellularia Californica | fatB | $C_{12:0}$ |
| AAC49269 (Q39513) | Cuphea hookeriana | fatB2 | $C_{8:0}$-$C_{10:0}$ |
| AAC49269; AAC72881 | Cuphea hookeriana | fatB3 | $C_{14:0}$-$C_{16:0}$ |
| AAC49151 (Q39473) | Cinnamonum camphorum | fatB | $C_{14:0}$ |
| CAA85388 | Arabidopsis thaliana | fatB | $C_{16:1}$ |
| NP_189147; NP_193041 | Arabidopsis thaliana | fatA | $C_{18:1}$ |
| CAC39106 | Bradyrhiizobium japonicum | fatA | $C_{18:1}$ |

TABLE 1-continued

Thioesterases

| GenBank accession number (UniProtKB/ Swiss-Prot) | Source organism | Gene | Preferential product produced |
|---|---|---|---|
| AAC72883 | Cuphea hookeriana | fatA | $C_{18:1}$ |
| AAL79361 | Helianthus annus | fatA1 | |
| JF338905 | Cocos nucifera | | $C_{12:0}$ |

The thioesterase may be a thioesterase that is naturally present in higher plants. Two families of acyl-ACP thioesterases are present in higher plants: the "Class I" acyl-ACP thioesterases encoded by FatA genes, which are responsible for cleaving long-chain (for example, $C_{16}$ and $C_{18}$) unsaturated fatty acids from acyl-ACP, and the "Class II" acyl-ACP thioesterases encoded by FatB genes, which are active on saturated fatty acyl chains, and which can be specific for medium-chain ($C_8$-$C_{14}$) acyl-ACPs or which can be active on both medium- and long-chain fatty acyl-ACPs. Non-limiting examples of thioesterases which are MCFA-specific and naturally present in plants, and hence suitable for (over)expression in the recombinant host cells described herein, are thioesterases encoded by FatB genes, or the thioesterases described for instance in Voelker et al. (1992 Science 257:72-74) and Jing et al. (2011 Biochemistry 12:44). The thioesterase may also be an engineered thioesterase as described for instance in Voelker et al. (1994 Journal of Bacteriology 176:7320-7327).

Depending on the α-olefin of interest, the expression of thioesterase enzymes may be either induced (by introduction into the host cell of an exogenous nucleic acid encoding said enzyme), stimulated (by overexpression of an endogenous gene encoding said enzyme) or attenuated (by modification of an endogenous gene encoding said enzyme).

In some situations, $C_{12}$ free fatty acids can be produced by expressing or overexpressing thioesterases that use $C_{12}$-ACP (for example, accession numbers Q41635 and JF338905) and attenuating thioesterases that produce non-$C_{12}$ fatty acids. In other instances, $C_{14}$ free fatty acids can be produced by attenuating endogenous thioesterases that produce non-$C_{14}$ fatty acids and (over)expressing the thioesterases that use $C_{14}$-ACP (for example, accession number Q39473).

Acetyl-CoA, malonyl-CoA, and free fatty acid overproduction can be verified using methods known in the art, for example, by using radioactive precursors, HPLC, and GC-MS subsequent to cell lysis.

For the production of $C_{11}$ α-olefins, the host cells are preferably modified by the introduction of an exogenous nucleic acid encoding a thioesterase having preferential hydrolase activity towards $C_{12}$ acyl-ACP substrate such as Q41635 or JF338905 and/or upregulating endogenous genes encoding a thioesterase having preferential hydrolase activity towards $C_{12}$ acyl-ACP, and optionally downregulating endogenous genes encoding thioesterases that produce non-$C_{12}$ fatty acids.

The medium-chain free fatty acids produced by the fatty acid enzymes in the host cells envisaged herein are the substrates of the decarboxylase enzymes described herein.

Accordingly, particularly preferred host cells for the production of medium-chain α-olefins are recombinant host cells comprising:

a recombinant nucleic acid encoding a thioesterase having preferential hydrolase activity towards medium-chain acyl-ACP substrate; and a recombinant nucleic acid encoding a medium-chain free fatty acid decarboxylase.

Particularly preferred host cells for the production of $C_{11}$ α-olefins are recombinant host cells comprising:
- a recombinant nucleic acid encoding a thioesterase having preferential hydrolase activity towards $C_{12}$ acyl-ACP substrate; and
- a recombinant nucleic acid encoding a $C_{12}$ free fatty acid decarboxylase.

In particular embodiments, the free fatty acid decarboxylase is an enzyme having at least about 70%, preferably at least about 80%, more preferably at least about 85%, 90% or 95%, even more preferably at least about 96%, 97%, 98% or 99% sequence identity to SEQ ID NO:4, SEQ ID NO:6, SEQ ID NO:8 or SEQ ID NO:13 and having medium-chain free fatty acid decarboxylase activity, in particular $C_8$-$C_{12}$ free fatty acid decarboxylase activity. In particular embodiments, the fatty acid decarboxylase is Sm46 (SEQ ID NO:8), Sm46-del29 (SEQ ID NO:13), Bs168 (SEQ ID NO:4) or Aa162 (SEQ ID NO:6) or a functional variant thereof since specific production of medium-chain α-olefins, in particular $C_7$-$C_{11}$ α-olefins, more particularly $C_{11}$ α-olefins, was shown herein for these enzymes. Accordingly, in particular embodiments, the application provides a genetically engineered host cell comprising a recombinant nucleic acid comprising a nucleotide sequence having at least about 70% or 75%, preferably at least about 80%, more preferably at least about 85%, 90% or 95%, even more preferably at least about 96%, 97%, 98% or 99% sequence identity to, SEQ ID NO:3, SEQ ID NO:5, SEQ ID NO:7, SEQ ID NO:9 or SEQ ID NO:10 and encoding an enzyme having medium-chain free fatty acid decarboxylase activity, in particular $C_8$-$C_{12}$ free fatty acid decarboxylase activity. In further particular embodiments, the recombinant nucleic acid comprises a nucleotide sequence having at least about 70% or 75%, preferably at least about 80%, more preferably at least about 85%, 90% or 95%, even more preferably at least about 96%, 97%, 98% or 99% sequence identity to SEQ ID NO:7, SEQ ID NO:9, SEQ ID NO:10, SEQ ID NO: 3 or SEQ ID NO: 5 and encodes an enzyme having decarboxylase activity for which $C_8$-$C_{12}$ free fatty acids, more particularly $C_{11}$ free fatty acids, are the preferred substrate. In preferred embodiments, the host cell comprises a recombinant nucleic acid encoding a polypeptide having an amino acid sequence comprising SEQ ID NO:8, SEQ ID NO:13, SEQ ID NO:4 or SEQ ID NO:6 or a functional variant thereof. In further embodiments, the genetically engineered host cell further comprises a recombinant nucleic acid encoding a thioesterase having preferential hydrolase activity towards medium-chain acyl-ACP substrate, preferably towards $C_8$-$C_{12}$ acyl-ACP substrate, more preferably towards $C_{12}$ acyl-ACP substrate.

In particular embodiments, where the above nucleotide sequences are endogenously expressed by the host cell of the invention, it is envisaged that expression of these sequences can be increased specifically so as to ensure commercially relevant medium-chain α-olefin production.

More particularly, in particular embodiments, the host cell is selected to have a high endogenous thioesterase activity. Methods of selecting cells having particular properties are known in the art.

Any cell that can be suitably transformed with and/or genetically engineered to ensure (over)expression of one or more of the described recombinant nucleic acids can be used in the context of the present invention. The host cells disclosed herein can be any prokaryotic or eukaryotic organism or cell. Non-limiting examples of host cells include plant cells, bacterial cells, yeast cells, fungal cells, and algal cells. In embodiments, the host cells are genetically engineered bacteria, or genetically engineered fungi, in particular yeasts, genetically engineered algae, or genetically engineered plant cells.

Preferably, the host cells are oleaginous host cells. For example, the host cell may be an oleaginous bacterium, an oleaginous fungus, oleaginous yeast or an oleaginous alga. Non-limiting examples of oleaginous yeasts include *Lipomyces starkeyi*, *Rhodosporidium toruloides*, *Rhodotorula glutinis*, and *Yarrowia lipolytica*. Non-limiting examples of oleaginous algae genera include *Botryococcus*, *Chaetoceros*, *Chlorella*, *Chlorococcum*, *Cylindrotheca*, *Dunaliella*, *Fistulifera*, *Isochrysis*, *Nannochloropsis*, *Neochloris*, *Nitzschia*, *Pavlova*, *Scenedesmus*, *Skeletonema*, *Stichococcus* and *Tetraselmis*.

Thus, the genetically engineered host cells disclosed herein comprise a recombinant nucleic acid encoding a medium-chain free fatty acid decarboxylase disclosed herein, and optionally one or more recombinant nucleic acids encoding a fatty acid enzyme, i.e. an enzyme involved in fatty acid synthesis. Additionally or alternatively the expression of one or more genes encoding enzymes involved in the production of fatty acids other than medium-chain free fatty acids may be suppressed, decreased or limited.

The methods for generating the genetically engineered host cells described herein involve standard genetic modifications, for which well-established methods are available to the skilled person.

Genetic engineering of the host cells to contain a recombinant nucleic acid encoding a polypeptide or a fatty acid enzyme as described herein is accomplished in one or more steps via the design and construction of appropriate vectors and transformation of the host cells with those vectors.

Electroporation and/or chemical (such as calcium chloride- or lithium acetate-based) transformation methods or *Agrobacterium tumefaciens*-mediated transformation methods as known in the art can be used.

The recombinant nucleic acid(s) encoding a decarboxylase enzyme and/or a fatty acid enzyme that may be provided in the host cells in the context of the present invention typically comprises a coding sequence encoding the decarboxylase enzyme and/or the fatty acid enzyme placed under the transcriptional control of one or more promoters and one or more terminators, both of which are functional in the host cell.

Promoter and terminator sequences may be native to the host cell or exogenous to the host cell. Useful promoter and terminator sequences include those that are highly identical (i.e. having an identities score of 90% or more, preferably 95% or more, most preferably 99% or more) in their functional portions compared to the functional portions of promoter and terminator sequences, respectively, that are native to the host cell, particularly when the insertion of the recombinant nucleic acid is targeted at a specific site in the host genome. The use of native (to the host) promoters and terminators, together with their respective upstream and downstream flanking regions, can permit the targeted integration of the recombinant nucleic acid into specific loci of the host genome.

Additionally or alternatively, the coding sequence may be native to the host cell or exogenous to the host cell.

Numerous vectors are known to practitioners skilled in the art, and selection of an appropriate vector is a matter of choice. The vectors can either be cut with particular restriction enzymes or used as circular DNA.

The vectors taught herein preferably comprise (a combination of) a recombinant nucleic acid as described herein. In particular, a vector comprises (a combination of) the coding sequence of a polypeptide or a fatty acid enzyme as described herein and associated promoter and terminator sequences. The vector may contain restriction sites of various types for linearization or fragmentation. Vectors may further contain a backbone portion (such as for propagation in *E. coli*) many of which are conveniently obtained from commercially available yeast or bacterial vectors. The vector preferably comprises one or more selection marker gene cassettes. A "selection marker gene" is one that encodes a protein needed for the survival and/or growth of the transformed cell in a selective culture medium. Typical selection marker genes encode proteins that (a) confer resistance to antibiotics or other toxins such as chloramphenicol, zeocin (sh ble gene from *Streptoalloteichus hindustanus*), genetecin, melibiase (MEL5), hygromycin (aminoglycoside antibiotic resistance gene from *E. coli*), ampicillin, tetracycline, or kanamycin (kanamycin resistance gene of Tn903), (b) complement auxotrophic deficiencies of the cell. Two prominent examples of auxotrophic deficiencies are the amino acid leucine deficiency (e.g. LEU2 gene) or uracil deficiency (e.g. URA3 gene). Cells that are orotidine-5'-phosphate decarboxylase negative (ura3-) cannot grow on media lacking uracil. Thus a functional URA3 gene can be used as a marker on a cell having a uracil deficiency, and successful transformants can be selected on a medium lacking uracil. Only cells transformed with the functional URA3 gene are able to synthesize uracil and grow on such medium. If the wild-type strain does not have a uracil deficiency (as is the case with *I. orientalis*, for example), an auxotrophic mutant having the deficiency must be made in order to use URA3 as a selection marker for the strain. Methods for accomplishing this are well known in the art. The selection marker cassette typically further includes a promoter and terminator sequence, operatively linked to the selection marker gene, and which are operable in the host.

Successful transformants can be selected for in known manner, by taking advantage of the attributes contributed by the marker gene, or by other characteristics (such as ability to produce α-olefins) contributed by the inserted recombinant nucleic acids. Screening can also be performed by PCR or Southern analysis to confirm that the desired insertions, and optionally deletions have taken place, to confirm copy number and to identify the point of integration of coding sequences into the host genome. Activity (such as α-olefin-producing activity) of the polypeptide encoded by the inserted coding sequence can be confirmed using known assay methods as described elsewhere herein.

Also disclosed herein are methods for obtaining a genetically engineered host cell capable of producing an α-olefin of interest as described herein, which method may comprise transforming a host cell with a recombinant nucleic acid encoding an enzyme having medium-chain free fatty acid decarboxylase activity as taught herein, more particularly a decarboxylase generating the α-olefin of interest and optionally one or more recombinant nucleic acids encoding a fatty acid enzyme as taught herein, more particularly a fatty acid enzyme involved in the synthesis of the substrate for the free fatty acid decarboxylase enzyme capable of generating the α-olefin of interest. In particular, the method may comprise the steps of:

a) transforming a host cell with a recombinant nucleic acid encoding an enzyme having medium-chain free fatty acid decarboxylase activity as taught herein and optionally one or more recombinant nucleic acids encoding a fatty acid enzyme as taught herein; and b) selecting a host cell capable of producing an α-olefin of interest.

In particular embodiments, the method further comprises modifying said host cell so as to reduce the endogenous production of olefins other than the α-olefin of interest.

As detailed above, different genetic modifications are envisaged herein which induce medium-chain α-olefin production and/or increase the yield of (one or more particular) medium-chain α-olefins in a host cell. Accordingly, the present invention also relates to the use of the genetically engineered host cells as described herein for the production of α-olefins, more particularly medium-chain α-olefins.

Producing α-Olefins Using Recombinant Host Cells

In a further aspect, the invention provides methods for the production of medium-chain α-olefins, more particularly $C_{11}$ α-olefins, which method comprises providing a genetically engineered host cell as described above and culturing said genetically engineered host cell in a culture medium so as to allow the production of medium-chain α-olefins. More particularly, the host cell is cultured under conditions suitable to ensure expression or overexpression of the enzyme having medium-chain free fatty acid decarboxylase activity envisaged herein and optionally one or more fatty acid enzyme(s) involved in the synthesis of the substrate of the enzyme having medium-chain free fatty acid decarboxylase activity.

In particular embodiments, the host cells ensure a rate of α-olefin production, more particularly medium-chain α-olefin production, which is sufficiently high to be industrially valuable. Indeed, the recombinant host cells disclosed herein may be capable of ensuring a high yield at limited production costs. Furthermore, they are capable of producing α-olefins of desired carbon chain length. Indeed, the decarboxylase enzymes envisaged herein preferably have substrate preference for a medium-chain free fatty acid, in particular a $C_8$-$C_{12}$ free fatty acid, more particularly $C_{12}$ free fatty acid. Also advantageously, the production of unwanted co-products such as hydroxyl fatty acids is minimal. Indeed, the polypeptides envisaged herein preferably have specific decarboxylase activity.

The recombinant host cells are cultured under conditions suitable for the production of medium-chain α-olefins by the host cells. More particularly this implies "conditions sufficient to allow (over)expression" of the recombinant nucleic acid encoding a decarboxylase enzyme, which means any condition that allows a host cell to (over)produce a medium-chain free fatty acid decarboxylase or a fatty acid enzyme as described herein. Suitable conditions include, for example, fermentation conditions. Fermentation conditions can comprise many parameters, such as temperature ranges, levels of aeration, and media composition. Each of these conditions, individually and in combination, allows the host cell to grow. To determine if conditions are sufficient to allow (over)expression, a host cell can be cultured, for example, for about 4, 8, 12, 18, 24, 36, or 48 hours. During and/or after culturing, samples can be obtained and analyzed to determine if the conditions allow (over)expression. For example, the host cells in the sample or the culture medium in which the host cells were grown can be tested for the presence of a desired product. When testing for the presence of a desired product, assays, such as, but not limited to, sodium dodecyl sulfate polyacrylamide gel electrophoresis (SDS-PAGE), TLC, HPLC, GC/FID, GC/MS, LC/MS, MS, can be used.

Exemplary culture media include broths or gels. Microorganisms are typically grown in a culture medium comprising a carbon source to be used for growth of the micro-organism. Exemplary carbon sources include carbohydrates, such as glucose, fructose, cellulose, or the like, that can be directly metabolized by a micro-organism. In addition, enzymes can be added to the culture medium to facilitate the mobilization (e.g., the depolymerization of starch or cellulose to fermentable sugars) and subsequent metabolism of the carbon source. A culture medium may optionally contain further nutrients as required by the particular strain, including inorganic nitrogen sources such as ammonia or ammonium salts, and the like, and minerals and the like.

Other growth conditions, such as temperature, cell density, and the like are generally selected to provide an economical process. Temperatures during each of the growth phase and the production phase may range from above the freezing temperature of the medium to about 50° C.

The culturing step of the methods of the invention may be conducted aerobically, anaerobically, or substantially anaerobically. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gasses.

The cultivation step of the methods described herein can be conducted continuously, batch-wise, or some combination thereof.

In particular embodiments, wherein phototrophic algae are used as host cells, the method for the production of medium-chain α-olefins may comprise providing algae genetically engineered to (over)produce medium-chain α-olefins as taught herein, and culturing said algae in photobioreactors or an open pond system using $CO_2$ and sunlight as feedstock.

In certain embodiments, the conditions suitable for the production of medium-chain α-olefins may further imply cultivating the host cells in a culture medium which comprises at least one fatty acid substrate, which is converted into an α-olefin by the decarboxylase encoded by the recombinant nucleic acid comprised in the host cell.

Preferably, the fatty acid substrate is a saturated free fatty acid substrate. Also preferably, the fatty acid substrate is a straight chain free fatty acid substrate. Also preferably, the fatty acid substrate is an even-numbered $C_8$-$C_{14}$ free fatty acid substrate (i.e. a free $C_8$, $C_{10}$, $C_{12}$, or $C_{14}$ free fatty acid substrate or any combination thereof), preferably an even-numbered $C_8$-$C_{12}$ free fatty acid substrate, more preferably a $C_{12}$ free fatty acid substrate.

Particularly intended herein is the production of medium-chain α-olefins, more particularly $C_{11}$ α-olefins. Medium-chain α-olefins, more particularly $C_{11}$ α-olefins can be obtained using a recombinant host cell described herein specifically modified for the production of medium-chain α-olefins, more particularly $C_{11}$ α-olefins.

In further embodiments, methods are provided for producing medium-chain α-olefins, more particularly $C_{11}$ α-olefins, which, in addition to the steps detailed above, further comprise the step of recovering the α-olefins from the host cell or the culture medium. Suitable purification can be carried out by methods known to the person skilled in the art such as by using lysis methods, extraction, ion exchange resins, electrodialysis, nanofiltration, etc.

Accordingly, methods are provided for the production of medium-chain α-olefins, more particularly $C_{11}$ α-olefins, which methods comprise the steps of:
(i) providing a genetically engineered host cell as described herein;
(ii) culturing the host cells in a culture medium under conditions suitable for the production of medium-chain α-olefins, and
(iii) recovering the α-olefins from the host cell or the culture medium.

In particular embodiments, wherein oleaginous yeasts are used as host cells, the method for the production of medium-chain α-olefins may comprise the following steps:
(i) providing oleaginous yeasts genetically engineered to (over)produce medium-chain α-olefins as taught herein;
(ii) culturing said oleaginous yeasts in fermenters; and
(iii) recovering the α-olefins from the oleaginous yeast or the culture medium.

In particular embodiments, wherein phototrophic algae are used as host cells, the method for the production of medium-chain α-olefins may comprise the following steps:
(i) providing algae genetically engineered to (over)produce medium-chain α-olefins as taught herein;
(ii) culturing said algae in photobioreactors or an open pond system using $CO_2$ and sunlight as feedstock; and
(iii) recovering the α-olefins from the algae or the culture medium.

In particular embodiments the host cells are cultivated under conditions which allow secretion of α-olefins into the environment.

Typically, in the methods for the production of medium chain α-olefins envisaged herein, the decarboxylase expressed by the host cell is not secreted by said host cell and the α-olefin is produced inside the host cell. However, in particular embodiments or for particular applications, it is of interest to ensure secretion of the decarboxylase by the host cells provided herein. This can be of interest where the enzyme is envisaged to be active upon secretion into its environment. A secretion signal sequence can be operably linked to the nucleic acid encoding the free fatty acid decarboxylase to this end. In this connection, "operably linked" denotes that the sequence encoding the secretion signal peptide and the sequence encoding the polypeptide to be secreted are connected in frame or in phase, such that upon expression the signal peptide facilitates the secretion of the polypeptide so-linked thereto.

Polypeptides

Also disclosed herein are enzymes having medium-chain free fatty acid decarboxylase activity. In particular embodiments, these polypeptides are encoded by nucleic acids and nucleotide sequences described herein. Accordingly, disclosed herein are polypeptides encoded by a nucleic acid comprising a nucleotide sequence having at least about 70% or 75%, preferably at least about 80%, more preferably at least about 85%, 90% or 95%, even more preferably at least about 96%, 97%, 98% or 99% sequence identity to SEQ ID NO: 3, SEQ ID NO: 5, SEQ ID NO: 7, SEQ ID NO:9 or SEQ ID NO:10 having medium-chain free fatty acid decarboxylase activity, in particular $C_8$-$C_{12}$ free fatty acid decarboxylase activity, preferably $C_{12}$ free fatty acid decarboxylase activity. Indeed, in particular embodiments, the enzymes having medium-chain free fatty acid decarboxylase activity, $C_8$-$C_{12}$ free fatty acid decarboxylase activity, preferably $C_{12}$ free fatty acid decarboxylase activity can be obtained by recombinant expression of said nucleic acids in a host cell. Methods for recombinant production of polypeptides are known in the art.

In particular embodiments, the polypeptides which are enzymes having medium-chain free fatty acid decarboxylase activity, in particular $C_8$-$C_{12}$ free fatty acid decarboxylase activity, more particularly $C_{12}$ free fatty acid decarboxylase activity, include polypeptides having an amino acid sequence comprising, consisting essentially of or consisting of, SEQ ID NO:4, SEQ ID NO:6, SEQ ID NO:8 or SEQ ID NO:13, and variants, including active fragments, of these polypeptides having medium-chain free fatty acid decarboxylase activity, in particular $C_8$-$C_{12}$ free fatty acid decarboxylase activity, more particularly $C_{12}$ free fatty acid decarboxylase activity. Preferred polypeptides are those consisting of the amino acid sequence of SEQ ID NO:4 (i.e. Bs168), SEQ ID NO:6 (i.e. Aa162), SEQ ID NO:8 (i.e. Sm46), or SEQ ID NO:13 (i.e. Sm46-del29) and functional variants of these polypeptides. Indeed, SEQ ID NO:8, and its active fragment of SEQ ID NO:13, are novel polypeptides provided herein having medium-chain free fatty acid decarboxylase activity, in particular $C_8$-$C_{12}$ free fatty acid decarboxylase activity, more particularly $C_{12}$ free fatty acid decarboxylase activity.

In particular embodiments, the polypeptides have decarboxylase activity with a preferred activity on medium-chain free fatty acids, in particular on a $C_8$-$C_{12}$ free fatty acid, more particularly on $C_{12}$ free fatty acids, i.e. the preferred substrate for these decarboxylase enzymes are medium-chain free fatty acids, in particular $C_8$-$C_{12}$ free fatty acids, more particularly $C_{12}$ free fatty acids. In particular embodiments, these enzymes have at least about 80%, 85%, 90% or 95%, even more preferably at least about 96%, 97%, 98% or 99% sequence identity to SEQ ID NO:8, SEQ ID NO:13, SEQ ID NO:4 or to SEQ ID NO: 6. Preferred enzymes comprise or consist of SEQ ID NO:8, SEQ ID NO:13, SEQ ID NO:4 or SEQ ID NO: 6 and functional variants thereof such as but not limited to an active fragment or variant thereof which maintains the activity of the enzyme comprising or consisting of SEQ ID NO:8, SEQ ID NO:13, SEQ ID NO:4 or SEQ ID NO: 6.

As used herein in connection to a decarboxylase enzyme, a "preferred substrate" refers to the free fatty acid for which the decarboxylase enzyme has the highest activity, i.e. when reacting with a number of free fatty acids, the decarboxylase enzyme has the highest activity when the substrate is the preferred free fatty acid substrate. The activity of a decarboxylase enzyme can be determined by measuring the concentration of the corresponding α-olefin product when the decarboxylase acid is reacted with a free fatty acid substrate. The α-olefin concentration in a reaction or culture medium can be measured by methods well known in the art, such as by GC/MS analysis. The substrate preference for a decarboxylase enzyme can hence be determined by calculating the conversion ratio of each free fatty acid substrate tested into corresponding α-olefin product, wherein the preferred substrate is the free fatty acid substrate with the highest conversion ratio. The substrate preference for a decarboxylase enzyme can also be determined by calculating the conversion ratio of each free fatty acid substrate tested, wherein the preferred substrate is the free fatty acid substrate with the highest conversion ratio. The "conversion ratio" or "substrate conversion ratio" means herein the ratio between consumed substrate (for instance fatty acid substrate concentration (e.g. in mM)) and produced reaction product(s) (for instance α-olefin concentration (e.g. in mM) and also potential co-product(s) is quantified (for instance hydroxyl fatty acid concentration (e.g. in mM)). The conversion ratio or conversion percentage for a specific reaction product can be calculated as the ratio between consumed substrate (for instance fatty acid substrate concentration (e.g. in mM)) and the specific reaction product produced (for instance α-olefin concentration (e.g. in mM).

Also envisaged herein are variant polypeptides of the polypeptides described herein. It is understood that the variant polypeptides described herein may have conservative or non-essential amino acid substitutions, which do not have a substantial effect on the polypeptide functions. Whether or not a particular substitution will be tolerated (i.e., will not adversely affect desired biological properties) can be determined as described in Bowie et al. (1990) (Science 247:1306 1310). A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Additional polypeptide variants are those in which additional amino acids are fused to the polypeptide, such as a secretion signal sequence, or a sequence which facilitates purification of the polypeptide.

Yet other polypeptide variants include functional or active fragments comprising at least about 5, 10, 15, 20, 25, 30, 35, 40, 50, 75, 100 or 150 consecutive amino acids, and which retain the same biological function as Bs168, Aa162, or Sm46 (e.g. retain olefin-producing activity, more particularly improved decarboxylase activity towards medium-chain free fatty acids, more preferably on $C_{12}$ FFA substrate). Exemplary functional or active fragments include without limitation truncated forms of the polypeptides described herein, which retain the decarboxylase activity of Bs168, Aa162, or Sm46. These functional or active fragments hence retain at least the decarboxylase catalytic domain of the polypeptide, i.e. the part of the polypeptide that is involved in the decarboxylase reaction. A particular example of such truncated form is the polypeptide having an amino acid sequence of SEQ ID NO:13 (encoded by the nucleotide sequence of SEQ ID NO:10), which polypeptide is a functional fragment of Sm46 wherein the 29 N-terminal amino acids were deleted.

Functional variants of the polypeptides described herein retain the decarboxylase activity of the polypeptides. Accordingly, the functional variants may comprise or consist of an amino acid sequence having at least about 70%, preferably at least about 80%, more preferably at least about 85%, 90% or 95%, even more preferably at least about 96%, 97%, 98% or 99% sequence identity in the decarboxylase catalytic domain of SEQ ID NO:4, SEQ ID NO:6, SEQ ID NO:8, or SEQ ID NO:13. The polypeptide variants may have an amino acid sequence substantially identical to SEQ ID NO:4, SEQ ID NO:6, SEQ ID NO:8, or SEQ ID NO:13 or they may have an amino acid sequence having at least about 70%, preferably at least about 80%, more preferably at least about 85%, 90% or 95%, even more preferably at least about 96%, 97%, 98% or 99% sequence identity to SEQ ID NO:4, SEQ ID NO:6, SEQ ID NO:8, or SEQ ID NO:13. The polypeptide variants, in particular the active or functional fragments, may have an amino acid sequence wherein the 40 or less, preferably 35 or less, more preferably 30 or less such as 29 or less, N-terminal amino acids of SEQ ID NO:4, SEQ ID NO:6, SEQ ID NO:8 or SEQ ID NO: 13 have been deleted.

The polypeptides disclosed herein have free fatty acid decarboxylase activity, in particular decarboxylase activity on $C_8$-$C_{14}$ free fatty acids, more particularly on even-numbered $C_8$-$C_{14}$ free fatty acids such as on $C_8$, $C_{10}$, $C_{12}$ and/or $C_{14}$ free fatty acids, even more particularly $C_8$-$C_{12}$ free fatty acid decarboxylase activity such as $C_{12}$ free fatty acid decarboxylase activity. Indeed, as shown in the experimental section, decarboxylase activity has been shown for OleT$_{JE}$, Bs168, Aa162, Sm46 or Sm46-del29, more particularly decarboxylase activity on $C_{12}$, $C_{14}$ and $C_{16}$ free fatty acids. The Sm46, Sm46-del29, Aa162 and Bs168 enzymes showed higher activity on $C_{12}$ free fatty acid, resulting in higher production of $C_{11}$ α-olefins.

Decarboxylase activity of a polypeptide can be assayed using routine methods. For example, the polypeptide can be contacted with a substrate, in particular a free fatty acid substrate, under conditions that allow the polypeptide to function. A decrease in the level of the substrate or an increase in the level of an α-olefin can be measured to determine decarboxylase or olefin-producing activity.

The polypeptides described herein may further catalyze the hydroxylation of fatty acids, in particular the α- and β-hydroxylation of fatty acids, as side reactions. Preferred polypeptides are those for which the decarboxylation activity is the dominant activity, i.e. which have specific decarboxylase activity. In preferred embodiments, the conversion of a free fatty substrate into hydroxy fatty acid, in particular α- and β-hydroxy fatty acid by the polypeptide is only marginal (such as less than 25%, preferably less than 20%, more preferably less than 10% of total products) as compared to the conversion of the fatty acid substrate into the corresponding α-olefin. In embodiments, the conversion percentage for hydroxy fatty acids is less than 25%, preferably less than 20%, more preferably less than 10%. The conversion percentage for hydroxy fatty acids can be calculated as the ratio between consumed substrate (for instance fatty acid substrate concentration (e.g. in mM)) and produced hydroxyl fatty acids (for instance hydroxyl fatty acid concentration (e.g. in mM)). Particular examples of polypeptides with specific decarboxylase activity are Sm46 or functional variants thereof, including active fragments thereof, such as the truncated form of Sm46 wherein the 29 N-terminal amino acids were deleted (i.e. the polypeptide encoded by the nucleotide sequence of SEQ ID NO:10 or the polypeptide of SEQ ID NO:13).

The polypeptides envisaged herein can be produced by recombinant expression in a host cell. In particular embodiments, the polypeptide is secreted by the host cell.

Production of α-Olefins

Also provided herein is the use of the medium-chain free fatty acid decarboxylase enzymes disclosed herein for the production of medium-chain α-olefins, more particularly $C_{11}$ α-olefins.

Some methods described herein relate to the production of medium-chain α-olefins, more particularly $C_{11}$ α-olefins, using a (purified) medium-chain free fatty acid decarboxylase enzyme disclosed herein and a free fatty acid substrate. Accordingly, disclosed herein is a method for the production of medium-chain α-olefins, more particularly $C_{11}$ α-olefins, comprising contacting a medium-chain free fatty acid decarboxylase enzyme with a suitable free fatty acid substrate so as to produce medium-chain α-olefins, more particularly $C_{11}$ α-olefins.

In particular embodiments, the medium-chain free fatty acid decarboxylase is a polypeptide having an amino acid sequence of SEQ ID NO:4, SEQ ID NO:6 SEQ ID NO:8 or SEQ ID NO:13 or a functional variant, including a functional or active fragment, of said polypeptide. In particular embodiments, the medium-chain free fatty acid decarboxylase is a polypeptide having an amino acid sequence having at least about 70%, preferably at least about 80%, more preferably at least about 85%, 90% or 95%, even more preferably at least about 96%, 97%, 98% or 99% sequence identity to SEQ ID NO:4, SEQ ID NO:6 SEQ ID NO:8 or SEQ ID NO:13. In particular embodiments, the enzyme has a preferred activity on medium-chain free fatty acids, more preferably on $C_8$-$C_{12}$ free fatty acids. Most particularly, the enzyme is a decarboxylase having preferred activity on $C_{12}$ free fatty acids and having an amino acid sequence having at least about 85%, 90% or 95%, even more preferably at least about 96%, 97%, 98% or 99% sequence identity to SEQ ID NO:8, SEQ ID NO:13, SEQ ID NO: 4 or SEQ ID NO: 6. In particular embodiments, the enzyme has 95% amino acid sequence identity to SEQ ID NO:8, SEQ ID NO:13, SEQ ID NO: 4 or SEQ ID NO: 6.

For example, a host cell can be genetically engineered to overexpress a medium-chain free fatty acid decarboxylase as disclosed herein. The recombinant host cell can be cultured under conditions sufficient to allow (over)expression of the decarboxylase. Cell-free extracts can then be generated using known methods. For example, the host cells can be lysed using detergents or by sonication. The overexpressed polypeptides can be purified using known methods, or the cell-free extracts can be used as such for the production of olefins. The host cells can also be genetically engineered to overexpress a medium-chain free fatty acid decarboxylase as disclosed herein and to secrete said polypeptide into the growth medium as described elsewhere. The secreted polypeptides can then be separated from the growth medium and optionally purified using known methods without the need for obtaining cell-free extracts.

Next, free fatty acid substrates can be added to the cell-free extracts or (purified) enzymes and maintained under conditions to allow conversion of the free fatty acid substrates to α-olefins. The α-olefins can then be separated and purified using known techniques.

Olefins having particular branching patterns, levels of saturation, and carbon chain length can be produced from free fatty acid substrates having those particular characteristics using the described methods. For example, the fatty acid substrate may be an unsaturated free fatty acid substrate (e.g. a monounsaturated free fatty acid substrate), or a saturated free fatty acid substrate. The fatty acid substrate may be a straight chain free fatty acid substrate, a branched chain free fatty acid substrate, or a free fatty acid substrate that includes a cyclic moiety.

Preferably, the fatty acid substrate is a saturated free fatty acid substrate. Also preferably, the fatty acid substrate is a straight chain free fatty acid substrate. Also preferably, the fatty acid substrate is an even-numbered $C_8$-$C_{14}$ free fatty acid substrate (i.e. a $C_8$, $C_{10}$, $C_{12}$ and/or $C_{14}$ free fatty acid substrate), more preferably an even-numbered $C_8$-$C_{12}$ free fatty acid substrate, most preferably a $C_{12}$ fatty acid substrate.

Particularly intended herein is the production of $C_{11}$ α-olefins. $C_{11}$ α-olefins can be obtained from a $C_{12}$ free fatty acid substrate using a $C_{12}$ free fatty acid decarboxylase enzyme described herein. As shown in the experimental section, Sm46, Sm46-del29, Bs168 and Aa162 specifically show decarboxylase activity on $C_{12}$ free fatty acid substrates, i.e. $C_{12}$ free fatty acid substrate is the preferred substrate for α-olefin production for Sm46, Sm46-del29, Bs168 and Aa162. Hence, in particular embodiments, the present invention relates to a method for the production of $C_{11}$ α-olefins, which method comprises contacting a $C_{12}$ free fatty acid decarboxylase encoded by a nucleic acid comprising a nucleotide sequence having at least about 70% or 75%, preferably at least about 80%, more preferably at least about 85%, 90% or 95%, even more preferably at least about 96%, 97%, 98% or 99% sequence identity to SEQ ID NO:7, SEQ ID NO:9, SEQ ID NO:10, SEQ ID NO:3 or SEQ ID NO:5. In embodiments, the method comprises contacting a polypeptide having an amino acid sequence comprising or consisting of SEQ ID NO:8, SEQ ID NO:13, SEQ ID NO:4 or SEQ ID NO:6 or a functional variant of said polypeptide, preferably a polypeptide consisting of SEQ ID NO:8, SEQ ID NO:13, SEQ ID NO:4 or SEQ ID NO:6, with a $C_{12}$ free fatty acid substrate, preferably dodecanoic acid (or lauric acid).

Also provided herein are medium-chain α-olefins, more particularly the $C_{11}$ α-olefins, obtainable by the methods disclosed herein.

Medium-Chain α-Olefins

Also disclosed herein are the medium-chain α-olefins, and compositions comprising medium-chain α-olefins more particularly the $C_{11}$ α-olefins, produced by the methods as herein described. The methods described herein advantageously result in the production of homogenous α-olefins, wherein the α-olefins produced have a uniform carbon chain length. These processes are hence more efficient than conventional processes which result in the production of mixture of α-olefins with different carbon chain length and which require separation of the different α-olefins for subsequent reactions.

Post-Production Processing

The produced α-olefins, more particularly medium-chain α-olefins such as $C_{11}$ α-olefins, can be used as or converted into a fuel, in particular a biofuel. These α-olefins, more particularly medium-chain α-olefins such as $C_{11}$ α-olefins, can also be used as starting material for the production of chemicals or personal care additives (e.g. polymers, surfactants, plastics, textiles, solvents, adhesives, etc.). They can also be used as feedstock for subsequent reactions, such as hydrogenation and/or oligomerization reactions, to make other products.

A further aspect of the invention relates to a method for the production of poly-α-olefins (PAO), said method comprising:
a) producing α-olefins, more particularly medium-chain α-olefins, according to a method disclosed herein;
b) oligomerizing the α-olefins produced in step a); and optionally
c) hydrogenating the oligomer produced in step b).

In particular embodiments, a method is provided for the production of $C_{33}$ PAOs, which comprises:
a) producing $C_{11}$ α-olefins according to a method disclosed herein;
b) trimerizing the $C_{11}$ α-olefins produced in step a); and optionally
c) hydrogenating the trimer produced in step b).

Oligomerization of medium-chain α-olefins in the presence of a catalyst is well known in the art. Catalysts that can be used for the oligomerization step are for example, but not limited to, $AlCl_3$, $BF_3$, $BF_3$ complexes for cationic oligomerization, and metal based catalysts like metallocenes.

Following the oligomerization step, residual unsaturation that is potentially present in the oligomers is saturated by catalytic hydrogenation resulting in saturated aliphatic hydrocarbons with one or more side branches.

The oligomers obtained by methods as described herein are known under the generic name of poly-α-olefins (PAO). The PAO production methods described herein advantageously result in the homogenous production of PAOs of a well-defined carbon chain length. Accordingly, the application also provides a composition of PAO's obtainable by a PAO production method described herein, characterized in that at least 50%, preferably at least 85% or 90%, more preferably at least 95% such as 96%, 97%, 98% or even 99% of the PAOs have a well-defined carbon chain length such as $C_{33}$ PAOs. Such a homogenous composition of poly-α-olefins has not previously been disclosed.

The methods provided herein allow obtaining a base oil with a well-defined viscosity. The PAOs, more particularly the $C_{33}$ PAOs, obtainable by a method as described herein can be used as base oils, which display very attractive viscosity indices, with the viscosity increasing with the number of carbons. These base oils can be used, together with additives and optionally other base oils, to formulate lubricants. In particular, PAOs with a number of carbons of about 30, more particularly 33 carbons, are preferred for automotive lubricants.

Accordingly, in a further aspect, the present invention relates to the use of the medium-chain free fatty acid decarboxylase enzymes and the recombinant host cells described herein for the industrial production of lubricants.

Also provided herein are lubricants comprising poly-α-olefins, more particularly lubricants comprising poly-α-olefins which contain a more homogenous composition of poly-α-olefins, more particularly a high concentration of poly-olefins of a well-defined length, such as those obtainable by a method as described herein. Indeed, the invention allows for the production of lubricants which are produced based on biosourced medium-chain alpha-olefins. More particularly, the invention allows for the provision of lubricants comprising poly-α-olefins, whereby at least 50%, preferably at least 85% or 90%, more preferably at least 95% such as 96%, 97%, 98% or even 99% of said poly-α-olefins are poly-α-olefins of a well defined carbon chain length, such as $C_{33}$ poly-α-olefins. Lubricants comprising such a homogenous composition of poly-α-olefins have not previously been disclosed.

Further disclosed herein are methods for the production of alkanes, said methods comprising: (a) production of α-olefins more particularly medium-chain α-olefins, according to a method disclosed herein; and (b) hydrogenation of the α-olefins obtained in step (a) to produce alkanes.

The present invention will now be further illustrated by means of the following non-limiting examples.

EXAMPLES

Example 1: Production of $C_{11}$ α-Olefins by $OleT_{JE}$, Sm46, Bs168 and Aa162

Material and Methods
Molecular Cloning

The genes encoding $OleT_{JE}$ (SEQ ID NO:1), Sm46 (SEQ ID NO:3), Bs168 (SEQ ID NO:5) and Aa162 (SEQ ID NO:7) were cloned into the NdeI/BamHI sites of the pET28a plasmid (Novagen, FIG. 2) by standard molecular biology techniques.

Protein Overexpression and Purification

E. coli BL21(DE3) cells (Novagen) carrying a recombinant plasmid or an empty PET28a plasmid (control) were cultured for several cycles to ensure best growth state at 37° C. in 10 mL LB medium supplemented with 50 µg/ml of kanamycin, followed by inoculation (1:100 ratio) into 50 mL fresh Terrific Broth medium containing 50 µg/ml of kanamycin, 1 mM thiamine, 10% glycerol and a rare salt solution (6750 mg/l $FeCl_3$, 500 mg/l $ZnCl_2$, 500 mg/l $CoCl_2$, 500 mg/l $Na_2MoO_4$, 250 mg/l $CaCl_2$, 465 mg/l $CuSO_4$, and 125 mg/l $H_3130_3$) at 37° C. Cells were grown at 37° C. for 3 to 4 h until the optical density at 600 nm ($OD_{600}$) reached 0.6 to 0.8, at which 0.2 or 0.4 mM isopropyl-β-$_D$-thiogalactopyranoside (IPTG) and 0.5 mM 5-aminolevulinic acid were added, followed by 18 h of cultivation at 16° C.

Figure 3:
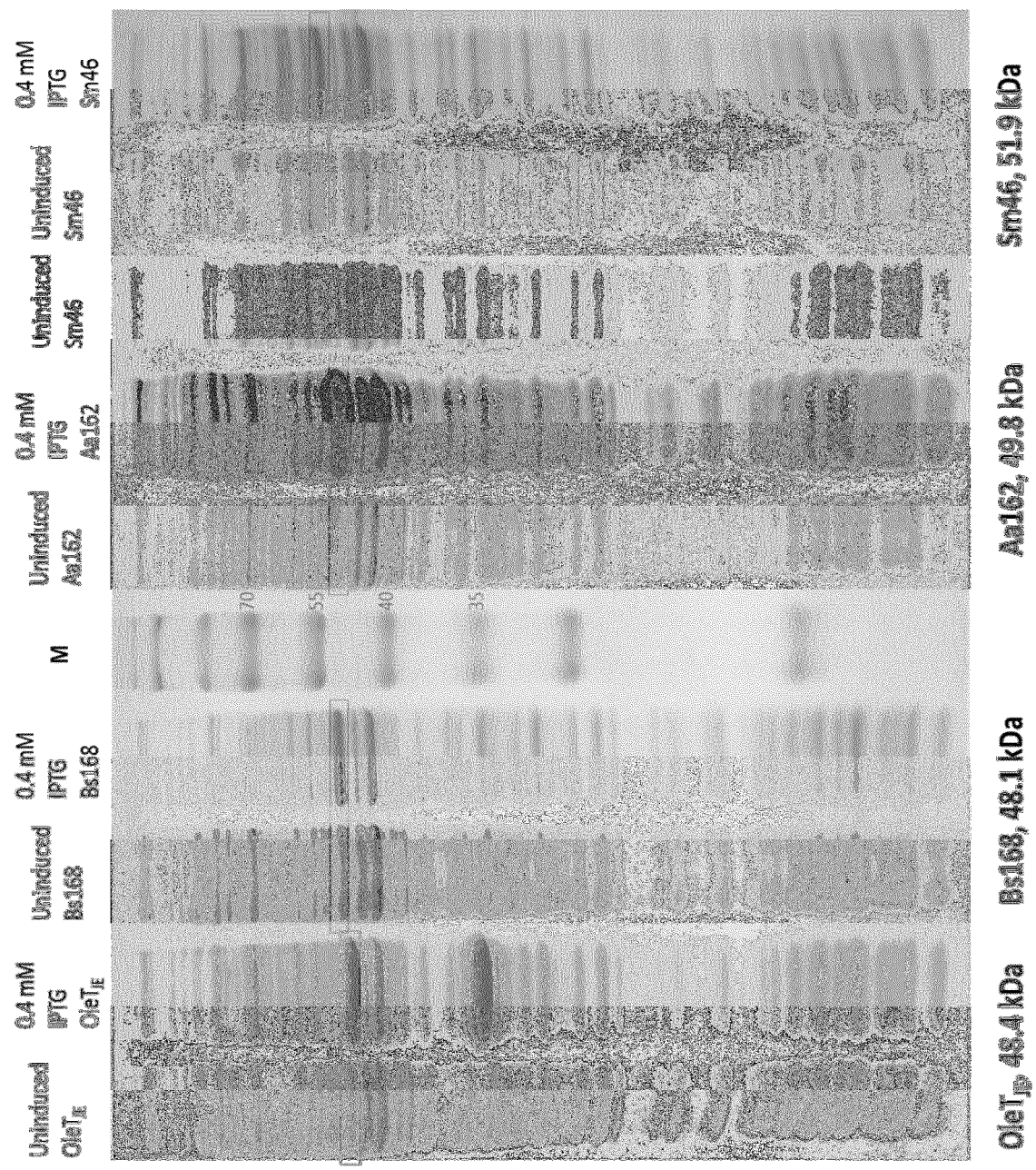
FIG. 3: Heterologous expression of genes encoding $OleT_{JE}$, Bs168, Aa162 and Sm46 in E. coli. SDS-PAGE analysis of lysates of E. coli cells carrying a recombinant plasmid comprising a gene encoding OleTJ, Bs168, Aa162 or Sm46, cultured under conditions to induce expression of the transgene (0.4 mM IPTG) or not (uninduced). M: protein marker.

Then, the cell cultures were recovered by centrifugation (at 4° C.) and re-suspended in 1.5 mL 50 mM Tris buffer, pH 7.5, containing 0.1 M NaCl. The re-suspended cell cultures were disrupted by sonication and centrifuged at 13,000×g for 30 min (4° C.). The supernatant was collected and the pellet was re-suspended in 1.5 mL 50 mM Tris buffer, pH 7.5, containing 0.1 M NaCl for further analysis. An SDS gel was run to check the expression of the genes using 15 µL of supernatant or pellet solution mixed with 5 µL of 4× loading buffer (FIG. 3).

The amount of total proteins within the supernatant was quantified using Pierce BCA kit according to the manufacturer's instructions.

In Vitro Enzymatic Assays

In vitro olefin biosynthesis was evaluated by adding to the supernatant a fatty acid substrate in DMSO to a final concentration of 0.2 mM (1:100 dilution) or 1 mM (1:10 dilution), and 500 µM $H_2O_2$. The reaction mixture was incubated at 28° C. for 2-3 h, or stopped using 50 µL of 10 M HCl at t=0, 15, 30, 60 and 120 min for a dynamic test. Then, $C_{16}$ fatty acid was added at a final concentration of 0.2 mM (1:100 dilution) as an internal standard. 300 µL reaction mixture of each reaction condition was extracted with equal volume of ethyl acetate, and the organic phase was analyzed for hydrocarbons by gas chromatography/mass spectrometry (GC/MS). In the meanwhile, undecene of different concentrations (0, 0.05 mM, 0.1 mM, 0.2 mM and 0.5 mM) were tested to produce a standard curve.

Results

Figure 4:
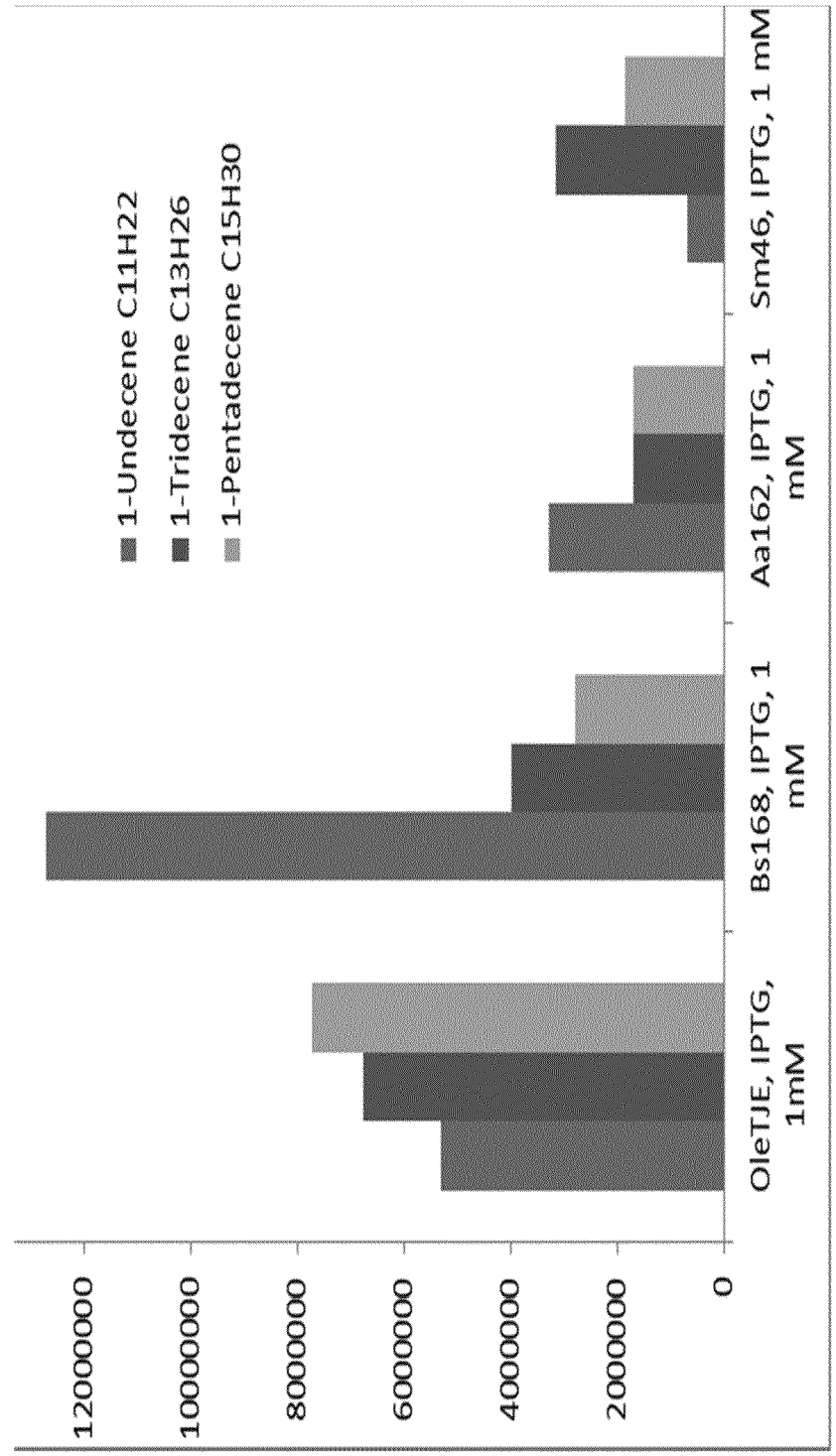
FIG. 4: In vitro production of α-olefins by $OleT_{JE}$, Bs168, Aa162 and Sm46. Genes encoding OleTJ, Bs168, Aa162 and Sm46 were recombinantly expressed in E. coli. The supernatant of the E. coli lysates was used in an in vitro assay for α-olefin biosynthesis in the presence of $C_{12}$, $C_{14}$ or $C_{16}$ fatty acid substrate (1 mM) and $H_2O_2$ (500 μM). $C_{11}$, $C_{13}$ and $C_{15}$ α-olefin production by the different enzymes is indicated as the area under the gas chromatographic (GC) peak.
Figure 7:
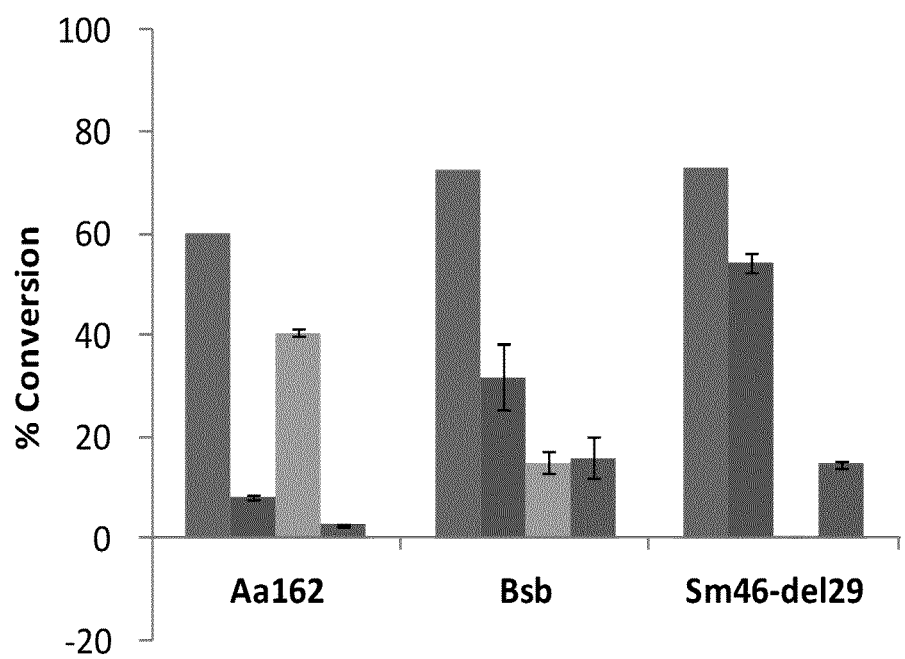
FIG. 7: In vitro production of α-olefins by Aa162, Bs168 and Sm46-del29. Recombinantly expressed and purified enzyme (0.2 μM) was used in an in vitro assay for α-olefin biosynthesis in the presence of $C_{14}$ fatty acid substrate. The conversion percentages are shown for, from left to right, $C_{14}$ free fatty acid substrate, $C_{13}$ α-olefin, α-hydroxy $C_{14}$ fatty acid, β-hydroxy $C_{14}$ fatty acid.

FIG. 4 shows fatty acid decarboxylase activity for all tested enzymes $OleT_{JE}$, Sm46, Bs168 and Aa162. Bs168 and Aa162 show preference for $C_{12}$ fatty acid substrate, thereby specifically producing $C_{11}$ α-olefins. In later experiments, Sm46 was also shown to have substrate preference for $C_{12}$ fatty acid substrate (data not shown).

Example 2: Production of α-Olefins by a Truncated Sm46 from *Staphylococcus Massiliensis*

The construct pET28b-Sm46 of Example 1 did show poor expression in E. coli BL21(DE3), which did not improve upon subcloning into another expression vector pCWori or optimization of the expression conditions. In order to maximize expression level and to assess potential of Sm46 as a decarboxylase enzyme with $C_{12}$ as preferred substrate, a truncated version of codon-optimized (for expression in E. coli) Sm46, Sm46-del29, was designed, which has the N-terminal 29 amino acids deleted, and the activity of the recombinant truncated Sm46-del29 was tested.

Material and Methods

Materials

Fatty acid substrates and terminal alkene authentic standards were purchased from TCI (Shanghai, China). Antibiotics were obtained from Solar-Bio (Beijing, China). Other chemicals were purchased from Sigma Aldrich (St. Louis, Mo., USA) or Ameresco (Solon, Ohio, USA). Molecular cloning kits, such as E.Z.N.A.™ Plasmid Miniprep Kit and Wizard SV Gel and PCR Clean-up System, were purchased from OMEGA Bio-Tek (Jinan, China) and Promega (Madison, Wis., USA) respectively. Oligonucleotides and codon-optimized gene were synthesized by Genewiz (Suzhou, China). The Pfu DNA polymerases and all restriction endonucleases were obtained from Takara (Dalian, China). Ni-NTA resin used for protein purification was from Qiagen (Valencia, Calif., USA); Millipore Amicon Ultra centrifugal filters (Billerica, Mass., USA) and PD-10 desalting columns were from GE Healthcare (Piscataway, N.J., USA).

Molecular Cloning Sm46-Del29 Gene

The 1,275 bp fragment of the truncated gene, Sm46-del29, was PCR-amplified from the initial construct of pET28b-Sm46 (see Example 1) using Pfu DNA polymerase and subsequently subcloned into pET28b vector at the Nde I/Xho I restriction sites. The sequences of primers used are as follows: GTCCATATGGCAAAAAAGCTGC-CTAAAGTG (Sm46-del29-F, forward primer, SEQ ID NO:11) and GTACTCGAGTTATTT-GCGGGCAACACGCGG (Sm46-del29-R, reverse primer, SEQ ID NO:12). All recombinant plasmid constructs were confirmed by DNA sequencing (Sangon Biotech, Shanghai, China). Upon sequence verification, plasmids were used to transform E. coli strain BL21 (DE3) for protein expression.

Heterologous Expression and Purification of Sm46-Del29

The E. coli BL21 (DE3) cells transformed with the recombinant pET28b-Sm46-de/29 plasmid were grown overnight at 37° C. with shaking at 220 rpm in LB medium containing 50 µg/ml kanamycin. The overnight culture was used as seed culture to inoculate (1:100 dilution) 1 to 3 liters of modified Terrific Broth containing 4% glycerol, 1 mM thiamine, trace metal and the corresponding antibiotics. Cells were then grown at 37° C. for 3 to 4 h until the optical density at 600 nm (OD600) reached ~0.6, at which point 5-aminolevulinic acid (0.5 mM final concentration) was supplemented and the expression of Sm46-del29 was induced by the addition of 0.2 mM isopropyl-β-D-thiogalactopyranoside (IPTG). Cells were then further cultured for 24 h at a reduced temperature of 18° C. before being harvested by centrifugation at 6000 rpm, 4° C. The cell pellet was frozen at −80° C. until required.

Purification of the His-tagged protein was carried out as described by Liu et al. (2014 Biotechnol. Biofuels 7:28) with minor modifications. All protein purification steps were performed at 4° C. Specifically, the cell pellets were thawed and re-suspended in 40 ml lysis buffer (50 mM $NaH_2PO_4$, 300 mM NaCl, 10% glycerol and 10 mM imidazole, pH 8.0) through vortexing. After cell disruption by ultrasonication, the cell lysate was centrifuged at 12,000×g for 30 min to remove cellular debris. To the clarified cell lysate, 1 ml of Ni-NTA resin was added and gently mixed at 4° C. for 1 h. The slurry was then loaded onto an empty column, and washed with approximately 100 ml of wash buffer (50 mM $NaH_2PO_4$, 300 mM NaCl, 10% glycerol and 20 mM imidazole, pH 8.0) until no proteins were detectable in flow-through. The bound target proteins were eluted with elution buffer (50 mM $NaH_2PO_4$, 300 mM NaCl, 10% glycerol and 250 mM imidazole, pH 8.0). The eluates were pooled and concentrated with an Amicon Ultra centrifugal filter, and buffer exchanged on a PD-10 column into storage buffer (50 mM NaH$_2$PO$_4$, 300 mM NaCl 10% glycerol, pH 7.4). The final purified protein was flash-frozen in liquid nitrogen and stored at −80° C. for later use.

UV-Visible Spectroscopy—Spectroscopic Characterization of Sm46-Del29

Analysis of the UV-visible spectroscopic properties of Sm46-del29 was performed on a Cary 60 UV-visible spectrophotometer (Varian, UK). The ferrous-CO complex of Sm46-del29 was prepared by slow bubbling of carbon monoxide gas into a solution of ferric P450, and subsequent reduction of the protein with sodium dithionite. The CO-bound reduced difference spectrum of the enzyme was obtained through recording the respective spectrum before and after the addition of sodium dithionite (Omura and Sato 1964. J Biol Chem 239:2379-2385, Amaya et al. 2016 J Inorg Biochem. 158:11-16).

In Vitro Enzymatic Assays

The fatty acid decarboxylation assays containing 1.0 µM Sm46-del29, 200 µM fatty acid substrate (from $C_8$ to $C_{20}$), 220 µM H$_2$O$_2$ in 200 µl of storage buffer were carried out at 28° C. for 2 h. Reactions were quenched by the addition of 20 µl of 10 M HCl. Heptadecanoic acid was added as internal standard and the mixture was extracted by 200 µl ethyl acetate. Following extraction, the organic phase was collected and analyzed by gas chromatography as described below.

Gas Chromatography (GC)

The GC analytical method for hydrocarbon and fatty acid samples was adapted from Guan et al. (2011 J Chromatogr A 1218:8289-8293). The analyses were performed on an Agilent 7890B gas chromatograph equipped with a capillary column HP-INNOWAX (Agilent Technologies, Santa Clara, Calif., USA; cross-linked polyethylene glycerol, i.d. 0.25 µm film thickness, 30 m by 0.25 mm). The helium flow rate was set to 1 ml per minute. The oven temperature was controlled initially at 40° C. for 4 min, then increased at the rate of 10° C. per min to 250° C., and held for 5 min. The injecting temperature was set to 280° C. with the injection volume of 1 µl under splitless injection conditions. The response factors between fatty acids and alkenes were determined by analyzing known authentic fatty acids ($C_{10}$-$C_{20}$), 1-alkenes ($C_9$-$C_{19}$) and 1-heptadecanoic acid standards as described in Liu et al. (2014 Biotechnol. Biofuels 7:28).

Results

The truncated variant of Sm46 (i.e. Sm46-del29) had decarboxylase activity and showed substrate preference for $C_{12}$ free fatty acid for α-olefin production among the tested fatty acid substrates (FIG. 6). Sm46-del29 was also able to decarboxylate $C_{10}$ free fatty acid, but technical problems (due to volatility) hindered detection of the formed $C_9$ α-olefin.

Example 3: Production of α-Olefins and Hydroxy Fatty Acids by Sm46-Del29, Bs168 and Aa162

Recombinantly expressed and purified Bs168 and Aa162 from Example 1 and Sm46-del29 of Example 2 were reacted with $C_{14}$ fatty acid and the products of decarboxylation ($C_{13}$ α-olefin) and hydroxylation (α-OH—$O_{14}$ fatty acid and β-OH—$C_{14}$ fatty acid) reactions were analyzed.

All enzymes tested were able to decarboxylate myristic acid ($C_{14}$), but also catalyzed α- and β-hydroxylation of myristic acid as side reactions. Fatty acid decarboxylation was the dominant reaction for all tested enzymes, but Sm46-del29 formed less hydroxy fatty acids, indicating that these enzymes have specific decarboxylase activity.

The invention claimed is:

1. A method for the production of $C_7$-$C_{11}$ α-olefins comprising culturing a recombinant host cell comprising a recombinant nucleic acid encoding a decarboxylase enzyme comprising the amino acid sequence of SEQ ID NO:13 under conditions suitable for the production of $C_7$ to $C_{11}$ α-olefins by said host cell, wherein the preferred substrate of said decarboxylase enzyme is an $C_8$-$C_{12}$ free fatty acid.

2. The method of claim 1, wherein said nucleic acid encoding a decarboxylase enzyme comprises a nucleotide sequence having at least about 75% sequence identity to SEQ ID NO:10 and wherein said recombinant nucleic acid ensures expression or overexpression of said decarboxylase.

3. The method according to claim 1, wherein $C_{12}$ free fatty acids are the preferred substrate of said decarboxylase, and wherein said α-olefins are $C_{11}$ α-olefins.

4. The method according to claim 1, wherein said host cell is cultivated in a medium comprising $C_8$-$C_{12}$ free fatty acids.

5. The method according to claim 1, wherein the host cell has further been genetically engineered to produce or overproduce $C_8$-$C_{12}$ free fatty acids.

6. The method according to claim 5, wherein the host cell comprises a recombinant nucleic acid encoding an enzyme involved in the production of free fatty acids with a carbon chain length between 8 and 12 free fatty acids.

7. The method according to claim 6, wherein the host cell comprises a recombinant nucleic acid encoding a thioesterase having activity on $C_8$ to $C_{12}$ acyl-ACP.

8. The method according to claim 1, wherein the host cell is an oleaginous host cell.

9. The method according to claim 1, wherein the host cell is selected from the group consisting of bacteria, yeasts, fungi, plants and algae.

10. The method according to claim 1, further comprising the step of recovering the α-olefins from the host cell or the culture medium.

11. A method for the production of poly-α-olefins comprising the following steps:
 i) producing $C_7$-$C_{11}$ α-olefins according to a method according to claim 1; and ii) performing an oligomerization reaction using the α-olefins obtained in step i) as monomer to produce an oligomer; and optionally, iii) hydrogenating the oligomer produced in step ii).

12. The method according to claim 11, wherein the poly-α-olefins are $C_{33}$ poly-α-olefins, wherein step i) comprises the production of $C_{11}$ α-olefins, and wherein the oligomerization reaction in step ii) is a trimerization reaction.

13. The method of claim 1, wherein said nucleic acid encoding a decarboxylase enzyme comprises a nucleotide sequence having at least about 80% sequence identity to SEQ ID NO:10 and wherein said recombinant nucleic acid ensures expression or overexpression of said decarboxylase.

14. The method of claim 1, wherein said nucleic acid encoding a decarboxylase enzyme comprises a nucleotide sequence having at least about 95%, sequence identity to SEQ ID NO:10 and wherein said recombinant nucleic acid ensures expression or overexpression of said decarboxylase.

15. The method according to claim 1, wherein said host cell is cultivated in a medium comprising $C_{12}$ free fatty acids.

16. The method according to claim 1, wherein the host cell has further been genetically engineered to produce or overproduce $C_{12}$ free fatty acids.

17. The method according to claim 5, wherein the host cell comprises a recombinant nucleic acid encoding an enzyme involved in the production of a $C_{12}$ free fatty acid.

18. The method according to claim 6, wherein the host cell comprises a recombinant nucleic acid encoding a thioesterase having activity on $C_{12}$ acyl-ACP.

* * * * *

SEQUENCE LISTING

<160> NUMBER OF SEQ ID NOS: 13

<210> SEQ ID NO 1
<211> LENGTH: 1269
<212> TYPE: DNA
<213> ORGANISM: Jeotgalicoccus sp.

<400> SEQUENCE: 1

```
atggcaacac ttaagaggga taagggctta gataatactt tgaaagtatt aaagcaaggt      60
tatctttaca caacaaatca gagaaatcgt ctaaacacat cagtttttcca aactaaagca     120 ctcggtggta aaccattcgt agttgtgact ggtaaggaag gcgctgaaat gttctacaac     180
aatgatgttg ttcaacgtga aggcatgtta ccaaaacgta tcgttaatac gcttttttggt     240 aaaggtgcaa tccatacggt agatggtaaa aaacacgtag acagaaaagc attgttcatg     300
agcttgatga ctgaaggtaa cttgaattat gtacgagaat taacgcgtac attatggcat     360
gcgaacacac aacgtatgga aagtatggat gaggtaaata tttaccgtga atctatcgta     420
ctacttacaa aagtaggaac acgttgggca ggcgttcaag caccacctga agatatcgaa     480
agaatcgcaa cagacatgga catcatgatc gattcattta gagcacttgg tggtgccttt     540
aaaggttaca aggcatcaaa agaagcacgt cgtcgtgttg aagattggtt agaagaacaa     600
attattgaga ctcgtaaagg gaatattcat ccaccagaag gtacagcact ttacgaattt     660
gcacattggg aagactactt aggtaaccca atggactcaa gaacttgtgc gattgactta     720
atgaacacat tccgcccatt aatcgcaatc aacagattcg tttcattcgg tttacacgcg     780
```

```
atgaacgaaa acccaatcac acgtgaaaaa attaaatcag aacctgacta tgcatataaa    840
ttcgctcaag aagttcgtcg ttactatcca ttcgttccat tccttccagg taaagcgaaa    900
gtagacatcg acttccaagg cgttacaatt cctgcaggtg taggtcttgc attagatgtt    960
tatggtacaa cgcatgatga atcactttgg gacgatccaa atgaattccg cccagaaaga   1020
ttcgaaactt gggacggatc accatttgac cttattccac aaggtggtgg agattactgg   1080
acaaatcacc gttgtgcagg tgaatggatc acagtaatca tcatggaaga aacaatgaaa   1140
tactttgcag aaaaaataac ttatgatgtt ccagaacaag atttagaagt ggacttaaac   1200
agtatcccag atacgttaa gagtggcttt gtaatcaaaa atgttcgcga agttgtagac    1260
agaacataa                                                           1269
```

<210> SEQ ID NO 2
<211> LENGTH: 422
<212> TYPE: PRT
<213> ORGANISM: Jeotgalicoccus sp.

<400> SEQUENCE: 2

```
Met Ala Thr Leu Lys Arg Asp Lys Gly Leu Asp Asn Thr Leu Lys Val
1               5                   10                  15

Leu Lys Gln Gly Tyr Leu Tyr Thr Thr Asn Gln Arg Asn Arg Leu Asn
                20                  25                  30

Thr Ser Val Phe Gln Thr Lys Ala Leu Gly Gly Lys Pro Phe Val Val
            35                  40                  45

Val Thr Gly Lys Glu Gly Ala Glu Met Phe Tyr Asn Asn Asp Val Val
        50                  55                  60

Gln Arg Glu Gly Met Leu Pro Lys Arg Ile Val Asn Thr Leu Phe Gly
65                  70                  75                  80

Lys Gly Ala Ile His Thr Val Asp Gly Lys His Val Asp Arg Lys
                85                  90                  95

Ala Leu Phe Met Ser Leu Met Thr Glu Gly Asn Leu Asn Tyr Val Arg
            100                 105                 110

Glu Leu Thr Arg Thr Leu Trp His Ala Asn Thr Gln Arg Met Glu Ser
        115                 120                 125

Met Asp Glu Val Asn Ile Tyr Arg Glu Ser Ile Val Leu Leu Thr Lys
    130                 135                 140

Val Gly Thr Arg Trp Ala Gly Val Gln Ala Pro Pro Glu Asp Ile Glu
145                 150                 155                 160

Arg Ile Ala Thr Asp Met Asp Ile Met Ile Asp Ser Phe Arg Ala Leu
                165                 170                 175

Gly Gly Ala Phe Lys Gly Tyr Lys Ala Ser Lys Glu Ala Arg Arg Arg
            180                 185                 190

Val Glu Asp Trp Leu Glu Glu Gln Ile Ile Glu Thr Arg Lys Gly Asn
        195                 200                 205

Ile His Pro Pro Glu Gly Thr Ala Leu Tyr Glu Phe Ala His Trp Glu
    210                 215                 220

Asp Tyr Leu Gly Asn Pro Met Asp Ser Arg Thr Cys Ala Ile Asp Leu
225                 230                 235                 240

Met Asn Thr Phe Arg Pro Leu Ile Ala Ile Asn Arg Phe Val Ser Phe
                245                 250                 255

Gly Leu His Ala Met Asn Glu Asn Pro Ile Thr Arg Glu Lys Ile Lys
            260                 265                 270

Ser Glu Pro Asp Tyr Ala Tyr Lys Phe Ala Gln Glu Val Arg Arg Tyr
        275                 280                 285
```

Tyr Pro Phe Val Pro Phe Leu Pro Gly Lys Ala Lys Val Asp Ile Asp
            290                 295                 300

Phe Gln Gly Val Thr Ile Pro Ala Gly Val Gly Leu Ala Leu Asp Val
305                 310                 315                 320

Tyr Gly Thr Thr His Asp Glu Ser Leu Trp Asp Pro Asn Glu Phe
            325                 330                 335

Arg Pro Glu Arg Phe Glu Thr Trp Asp Gly Ser Pro Phe Asp Leu Ile
            340                 345                 350

Pro Gln Gly Gly Gly Asp Tyr Trp Thr Asn His Arg Cys Ala Gly Glu
        355                 360                 365

Trp Ile Thr Val Ile Ile Met Glu Glu Thr Met Lys Tyr Phe Ala Glu
        370                 375                 380

Lys Ile Thr Tyr Asp Val Pro Glu Gln Asp Leu Glu Val Asp Leu Asn
385                 390                 395                 400

Ser Ile Pro Gly Tyr Val Lys Ser Gly Phe Val Ile Lys Asn Val Arg
            405                 410                 415

Glu Val Val Asp Arg Thr
            420

<210> SEQ ID NO 3
<211> LENGTH: 1254
<212> TYPE: DNA
<213> ORGANISM: Bacillus subtilis

<400> SEQUENCE: 3

```
atgaatgagc agattccaca tgacaaaagt ctcgataaca gtctgacact gctgaaggaa      60
gggtatttat ttattaaaaa cagaacagag cgctacaatt cagatctgtt tcaggcccgt     120
ttgttgggaa aaactttat ttgcatgact ggcgctgagg cggcgaaggt gttttatgat     180
acggatcgat tccagcggca gaacgctttg cctaagcggg tgcagaaatc gctgtttggt     240
gttaatgcga ttcagggaat ggatggcagc gcgcatatcc atcggaagat gcttttctg     300
tcattgatga caccgccgca tcaaaaacgt ttggctgagt tgatgacaga ggagtggaaa     360
gcagcagtca agatgggaa gaaggcagat gaggttgtgt atttgaaga agcaaaagaa     420
atcctgtgcc gggtagcgtg ctattgggca ggtgttccgt gaaggaaac ggaagtcaaa      480
gagagagcgg atgacttcat tgacatggtc gacgcgttcg gtgctgtggg accgcggcat     540
tggaaaggaa gaagagcaag gccgcgtgcg gaagagtgga ttgaagtcat gattgaagat     600
gctcgtgccg gcttgctgaa aacgacttcc ggaacagcgc tgcatgaaat ggcttttcac     660
acacaagaag atggaagcca gctggattcc cgcatggcag ccattgagct gattaatgta     720
ctgcggccta ttgtcgccat ttcttacttt ctggtgtttt cagctttggc gcttcatgag     780
catccgaagt ataaggaatg gctgcggtct ggaaacagcc gggaaagaga atgtttgtg     840
caggaggtcc gcagatatta tccgttcggc ccgttttag gggcgcttgt caaaaaagat     900
tttgtatgga ataactgtga gtttaagaag ggcacatcgg tgctgcttga tttatatgga     960
acgaaccacg accctcgtct atgggatcat cccgatgaat ccggccgga acgatttgcg    1020
gagcgggaag aaaatctgtt tgatatgatt cctcaaggcg gggggcacgc cgagaaaggc    1080
caccgctgtc aggggaagg cattacaatt gaagtcatga agcgagcct ggatttcctc     1140
gtccatcaga ttgaatacga tgttccggaa caatcactgc attacagtct cgccagaatg    1200
ccatcattgc tgaaagcgg cttcgtaatg agcggaatca gacgaaaaag ttaa            1254
```

```
<210> SEQ ID NO 4
<211> LENGTH: 417
<212> TYPE: PRT
<213> ORGANISM: Bacillus subtilis

<400> SEQUENCE: 4

Met Asn Glu Gln Ile Pro His Asp Lys Ser Leu Asp Asn Ser Leu Thr
  1               5                  10                  15

Leu Leu Lys Glu Gly Tyr Leu Phe Ile Lys Asn Arg Thr Glu Arg Tyr
             20                  25                  30

Asn Ser Asp Leu Phe Gln Ala Arg Leu Leu Gly Lys Asn Phe Ile Cys
         35                  40                  45

Met Thr Gly Ala Glu Ala Lys Val Phe Tyr Asp Thr Asp Arg Phe
     50                  55                  60

Gln Arg Gln Asn Ala Leu Pro Lys Arg Val Gln Lys Ser Leu Phe Gly
 65                  70                  75                  80

Val Asn Ala Ile Gln Gly Met Asp Gly Ser Ala His Ile His Arg Lys
                 85                  90                  95

Met Leu Phe Leu Ser Leu Met Thr Pro Pro His Gln Lys Arg Leu Ala
            100                 105                 110

Glu Leu Met Thr Glu Glu Trp Lys Ala Ala Val Thr Arg Trp Glu Lys
        115                 120                 125

Ala Asp Glu Val Val Leu Phe Glu Glu Ala Lys Glu Ile Leu Cys Arg
    130                 135                 140

Val Ala Cys Tyr Trp Ala Gly Val Pro Leu Lys Glu Thr Glu Val Lys
145                 150                 155                 160

Glu Arg Ala Asp Asp Phe Ile Asp Met Val Asp Ala Phe Gly Ala Val
                165                 170                 175

Gly Pro Arg His Trp Lys Gly Arg Arg Ala Arg Pro Arg Ala Glu Glu
            180                 185                 190

Trp Ile Glu Val Met Ile Glu Asp Ala Arg Ala Gly Leu Leu Lys Thr
        195                 200                 205

Thr Ser Gly Thr Ala Leu His Glu Met Ala Phe His Thr Gln Glu Asp
    210                 215                 220

Gly Ser Gln Leu Asp Ser Arg Met Ala Ala Ile Glu Leu Ile Asn Val
225                 230                 235                 240

Leu Arg Pro Ile Val Ala Ile Ser Tyr Phe Leu Val Phe Ser Ala Leu
                245                 250                 255

Ala Leu His Glu His Pro Lys Tyr Lys Glu Trp Leu Arg Ser Gly Asn
            260                 265                 270

Ser Arg Glu Arg Glu Met Phe Val Gln Glu Val Arg Tyr Tyr Pro
    275                 280                 285

Phe Gly Pro Phe Leu Gly Ala Leu Val Lys Lys Asp Phe Val Trp Asn
    290                 295                 300

Asn Cys Glu Phe Lys Lys Gly Thr Ser Val Leu Leu Asp Leu Tyr Gly
305                 310                 315                 320

Thr Asn His Asp Pro Arg Leu Trp Asp His Pro Asp Glu Phe Arg Pro
                325                 330                 335

Glu Arg Phe Ala Glu Arg Glu Asn Leu Phe Asp Met Ile Pro Gln
            340                 345                 350

Gly Gly Gly His Ala Glu Lys Gly His Arg Cys Pro Gly Glu Gly Ile
        355                 360                 365

Thr Ile Glu Val Met Lys Ala Ser Leu Asp Phe Leu Val His Gln Ile
    370                 375                 380
```

```
Glu Tyr Asp Val Pro Glu Gln Ser Leu His Tyr Ser Leu Ala Arg Met
385                 390                 395                 400

Pro Ser Leu Pro Glu Ser Gly Phe Val Met Ser Gly Ile Arg Arg Lys
            405                 410                 415

Ser

<210> SEQ ID NO 5
<211> LENGTH: 1311
<212> TYPE: DNA
<213> ORGANISM: Alicyclobacillus acidocaldarius

<400> SEQUENCE: 5
atgaatcagt gcattccgcg cgatcgaacg tttgacagca gcctcgcctt gataaaggaa      60
gggtatttgt tcatcaaaaa tcgagttgat caataccaat ccgacatctt cgaagcgcgt     120
ctcctcctgg aaaatgtggt atgcatgcac ggagcagagg cggcaaaact cttctacaat     180
acggaactgt tcaacgcca aggtgctctt ccgaagcggg ttcaaaagac gcttttcgga      240
gaaaacgcca tccaaaccct tgatggtaca gcgcatcttc accgtaagca gctgtttctg     300
tcgttgttga cgccggatca agaaaaatcc cttgcgacgc tcgcgacaac gcagtggagg     360
gagtgcgcga aggtatggga gaacgcggat agggttgtgc tatttgaaga ggccaagcgg     420
atgttatgtc ggatcgcatg tcagtggacc ggggttccgc tggatgaatc ggaggtgtca     480
aagcgggccg acgattttgg ggcgatggtg gacgcgtttg gagcggttgg tccgcgacat     540
tggaaaggcc ggagagctcg ggccagagca gaagcatggc tccggcagat gattgacgag     600
atacgaatcg gattgcgtag tgtagatgaa catacgccgc tccatgtggt ggccttttgg     660
cgtgacgtga atggaaacct cttggatgct cagatggttg caatcgagtt aatcaatctg     720
ctacgaccca tcgtagctat ttctactttc atcacgtttt cagccctggc cctgcacgaa     780 caccccgacat ggcgagaccg attgaaggcg cgcaatgaag cggatatcga tgtgtttgtg    840
caagaggttc gtcgctacta tccgttcgcg ccatttctcg gtgccagagt gaaaaaggat     900
tttgtgtgga gggatacga atttaaaaga gggaccctcg tgttgctgga tgtgtatgga     960
acccatcatg atgcccgcct ctgggattcc ccaaatgagt tcgacccga acgattcatg    1020 agaaaaacag ttgggccgtt tgatttgatt cctcaaggtg aggggactc tcacaccggt    1080 catcgttgcc ctggtgaagg cgccaccatc gagattatga aggcgagcgt ggatttttctg    1140 gttaaccaaa ttgacttcga agtgcccgct caggacctca gttacagatt ggatgttatg    1200
ccgacgttgc caaagagcgg atttgtgctg acccatgttc atcggaagtt catagcttct    1260
ccgaccattg ctacacctaa tggttctgaa gctcttcctt cagaagtcta a             1311

<210> SEQ ID NO 6
<211> LENGTH: 436
<212> TYPE: PRT
<213> ORGANISM: Alicyclobacillus acidocaldarius

<400> SEQUENCE: 6

Met Asn Gln Cys Ile Pro Arg Asp Arg Thr Phe Asp Ser Ser Leu Ala
1               5                   10                  15

Leu Ile Lys Glu Gly Tyr Leu Phe Ile Lys Asn Arg Val Asp Gln Tyr
            20                  25                  30

Gln Ser Asp Ile Phe Glu Ala Arg Leu Leu Leu Glu Asn Val Val Cys
        35                  40                  45

Met His Gly Ala Glu Ala Ala Lys Leu Phe Tyr Asn Thr Glu Leu Phe
    50                  55                  60
```

Gln Arg Gln Gly Ala Leu Pro Lys Arg Val Gln Lys Thr Leu Phe Gly
 65                  70                  75                  80

Glu Asn Ala Ile Gln Thr Leu Asp Gly Thr Ala His Leu His Arg Lys
                 85                  90                  95

Gln Leu Phe Leu Ser Leu Leu Thr Pro Asp Gln Glu Lys Ser Leu Ala
             100                 105                 110

Thr Leu Ala Thr Thr Gln Trp Arg Glu Cys Ala Lys Val Trp Glu Asn
         115                 120                 125

Ala Asp Arg Val Val Leu Phe Glu Glu Ala Lys Arg Met Leu Cys Arg
130                 135                 140

Ile Ala Cys Gln Trp Thr Gly Val Pro Leu Asp Glu Ser Glu Val Ser
145                 150                 155                 160

Lys Arg Ala Asp Asp Phe Gly Ala Met Val Asp Ala Phe Gly Ala Val
                 165                 170                 175

Gly Pro Arg His Trp Lys Gly Arg Arg Ala Arg Ala Arg Ala Glu Ala
             180                 185                 190

Trp Leu Arg Gln Met Ile Asp Glu Ile Arg Ile Gly Leu Arg Ser Val
         195                 200                 205

Asp Glu His Thr Pro Leu His Val Val Ala Phe Trp Arg Asp Val Asn
210                 215                 220

Gly Asn Leu Leu Asp Ala Gln Met Val Ala Ile Glu Leu Ile Asn Leu
225                 230                 235                 240

Leu Arg Pro Ile Val Ala Ile Ser Thr Phe Ile Thr Phe Ser Ala Leu
                 245                 250                 255

Ala Leu His Glu His Pro Thr Trp Arg Asp Arg Leu Lys Ala Arg Asn
             260                 265                 270

Glu Ala Asp Ile Glu Met Phe Val Gln Glu Val Arg Arg Tyr Tyr Pro
         275                 280                 285

Phe Ala Pro Phe Leu Gly Ala Arg Val Lys Lys Asp Phe Val Trp Arg
290                 295                 300

Gly Tyr Glu Phe Lys Arg Gly Thr Leu Val Leu Leu Asp Val Tyr Gly
305                 310                 315                 320

Thr His His Asp Ala Arg Leu Trp Asp Ser Pro Asn Glu Phe Arg Pro
                 325                 330                 335

Glu Arg Phe Met Arg Lys Thr Val Gly Pro Phe Asp Leu Ile Pro Gln
             340                 345                 350

Gly Gly Gly Asp Ser His Thr Gly His Arg Cys Pro Gly Glu Gly Ala
         355                 360                 365

Thr Ile Glu Ile Met Lys Ala Ser Val Asp Phe Leu Val Asn Gln Ile
         370                 375                 380

Asp Phe Glu Val Pro Ala Gln Asp Leu Ser Tyr Arg Leu Asp Val Met
385                 390                 395                 400

Pro Thr Leu Pro Lys Ser Gly Phe Val Leu Thr His Val His Arg Lys
                 405                 410                 415

Phe Ile Ala Ser Pro Thr Ile Ala Thr Pro Asn Gly Ser Glu Ala Leu
             420                 425                 430

Pro Ser Glu Val
         435

<210> SEQ ID NO 7
<211> LENGTH: 1362
<212> TYPE: DNA
<213> ORGANISM: Staphylococcus massiliensis

<400> SEQUENCE: 7

```
atgtttgtag attcgatact tgtgttaaga ttaaatttat taaaaacggg tatacaatta      60
gaaatgaaaa atgggggaat caaagtggca aagaaactac ctaaggttaa aggcctagat     120
aacacagtag acattattaa aggcgggtat acatacgtac ctggcaaatt agaagaattt     180
gattctaaag catttgaagt acgcgcatta ggcggtaaga aaattgctgt tatgagcggt     240
aaagaagcgg cagaaatttt ctatgataat gaaaaaatgg aaagacaagg tactttacca     300
aaacgtatcg taaacacttt atttggtaaa ggtgcaattc atacaactgc tggtaagaag     360
cacgttgacc gtaaagcttt atttatgtca cttatgacag atgaaaatct taactactta     420
cgtgaattaa cacgtaatta ttggttcatg aatactgaac gtatgcaaag catggataaa     480
gttaacgtat ataacgaatc aatttatatg ttaactaaaa tcggcttccg ttgggctggt     540
atcatccaaa cgcctgaaga agcagaacaa aatgcgaaag acatggatac tatgattaac     600
tcattcgtat ctttaggttc agcttacaaa ggttataaga agctaaaaaa agcacgtaaa     660
cgtgttgaag atttcttaga aaacaaatt atcgatgtgc gtaaaggtaa attacaccct     720
gaagaaggta ctgcgttata cgaattcgcg cattgggaag atttaaacga taacccaatg     780
gattctcact tatgtgcagt agacttaatg aacgttgtgc gcccattagc tgcaatcaac     840
cgtttcatca gctatggtgt taaagtatta atcgaattcg atcaagaaaa agaaaaatta     900
cgtcttgaaa ataatgaaga ctatgcgtat aaattcgctc aagaagtacg tcgtatcttc     960
ccattcgtac atacttacc aggtagagca gctgttgatt tagaatatga cggctacaaa    1020
atccctgcag gtatgatgac agcattagat gtttatggta cgacacatga tgaagattta    1080
tgggaaaacc cagaccaatt caatcctaac cgttttgata actgggacgg tagcccattc    1140
gacttaattc cacaaggtgg cggtgacttc tatacgaacc acagatgtgc tggtgagtgg    1200
atcacagtta tcattatgga agaaacaatg aaatatttcg cgaataagat tgaatttgat    1260
gtaccgtctc aagatttatc agttaagctt gataaaattac caggtaacgt aacaagcggt    1320
acaatcatta gtaatgtacg tccacgtgtt gcgcgtaaat aa                        1362
```

<210> SEQ ID NO 8
<211> LENGTH: 453
<212> TYPE: PRT
<213> ORGANISM: Staphylococcus massiliensis

<400> SEQUENCE: 8

```
Met Phe Val Asp Ser Ile Leu Val Leu Arg Leu Asn Leu Leu Lys Thr
1               5                   10                  15
Gly Ile Gln Leu Glu Met Lys Asn Gly Gly Ile Lys Val Ala Lys Lys
            20                  25                  30
Leu Pro Lys Val Lys Gly Leu Asp Asn Thr Val Asp Ile Ile Lys Gly
        35                  40                  45
Gly Tyr Thr Tyr Val Pro Gly Lys Leu Glu Glu Phe Asp Ser Lys Ala
    50                  55                  60
Phe Glu Val Arg Ala Leu Gly Gly Lys Lys Ile Ala Val Met Ser Gly
65                  70                  75                  80
Lys Glu Ala Ala Glu Ile Phe Tyr Asp Asn Glu Lys Met Glu Arg Gln
                85                  90                  95
Gly Thr Leu Pro Lys Arg Ile Val Asn Thr Leu Phe Gly Lys Gly Ala
            100                 105                 110
Ile His Thr Thr Ala Gly Lys Lys His Val Asp Arg Lys Ala Leu Phe
        115                 120                 125
```

Met Ser Leu Met Thr Asp Glu Asn Leu Asn Tyr Leu Arg Glu Leu Thr
130                 135                 140

Arg Asn Tyr Trp Phe Met Asn Thr Glu Arg Met Gln Ser Met Asp Lys
145                 150                 155                 160

Val Asn Val Tyr Asn Glu Ser Ile Tyr Met Leu Thr Lys Ile Gly Phe
            165                 170                 175

Arg Trp Ala Gly Ile Ile Gln Thr Pro Glu Glu Ala Glu Gln Asn Ala
        180                 185                 190

Lys Asp Met Asp Thr Met Ile Asn Ser Phe Val Ser Leu Gly Ser Ala
    195                 200                 205

Tyr Lys Gly Tyr Lys Lys Ala Lys Lys Ala Arg Lys Arg Val Glu Asp
210                 215                 220

Phe Leu Glu Lys Gln Ile Ile Asp Val Arg Lys Gly Lys Leu His Pro
225                 230                 235                 240

Glu Glu Gly Thr Ala Leu Tyr Glu Phe Ala His Trp Glu Asp Leu Asn
            245                 250                 255

Asp Asn Pro Met Asp Ser His Leu Cys Ala Val Asp Leu Met Asn Val
        260                 265                 270

Val Arg Pro Leu Ala Ala Ile Asn Arg Phe Ile Ser Tyr Gly Val Lys
    275                 280                 285

Val Leu Ile Glu Phe Asp Gln Glu Lys Glu Lys Leu Arg Leu Glu Asn
290                 295                 300

Asn Glu Asp Tyr Ala Tyr Lys Phe Ala Gln Glu Val Arg Arg Ile Phe
305                 310                 315                 320

Pro Phe Val Pro Tyr Leu Pro Gly Arg Ala Ala Val Asp Leu Glu Tyr
            325                 330                 335

Asp Gly Tyr Lys Ile Pro Ala Gly Met Met Thr Ala Leu Asp Val Tyr
        340                 345                 350

Gly Thr Thr His Asp Glu Asp Leu Trp Glu Asn Pro Asp Gln Phe Asn
    355                 360                 365

Pro Asn Arg Phe Asp Asn Trp Asp Gly Ser Pro Phe Asp Leu Ile Pro
370                 375                 380

Gln Gly Gly Gly Asp Phe Tyr Thr Asn His Arg Cys Ala Gly Glu Trp
385                 390                 395                 400

Ile Thr Val Ile Ile Met Glu Glu Thr Met Lys Tyr Phe Ala Asn Lys
            405                 410                 415

Ile Glu Phe Asp Val Pro Ser Gln Asp Leu Ser Val Lys Leu Asp Lys
        420                 425                 430

Leu Pro Gly Asn Val Thr Ser Gly Thr Ile Ile Ser Asn Val Arg Pro
    435                 440                 445

Arg Val Ala Arg Lys
    450

<210> SEQ ID NO 9
<211> LENGTH: 1359
<212> TYPE: DNA
<213> ORGANISM: Artificial Sequence
<220> FEATURE:
<223> OTHER INFORMATION: codon-optimized nucleotide sequence encoding
      Sm46

<400> SEQUENCE: 9
ttcgtggata gcattctggt tctgcgcctg aacctgctga agacaggcat ccagctggag      60
atgaagaacg gtggcatcaa agtggcaaaa aagctgccta agtgaaaggt ctggacaac      120

-continued

| | |
|---|---|
| accgtggaca tcatcaaggg tggctatacc tacgtgcctg gcaaactgga ggagttcgac | 180 |
| agcaaagcat tcgaagtgcg cgccctgggt ggcaagaaga tcgcagtgat gagcggcaag | 240 |
| gaagccgccg agatttttta tgataacgaa aaaatggagc gtcagggtac cctgccgaag | 300 |
| cgcatcgtga acacactgtt cggtaaaggc gccattcata ccaccgccgg caagaaacat | 360 |
| gtggatcgca aggcactgtt catgagtctg atgaccgatg aaaatttaaa ttatctgcgc | 420 |
| gaactgacac gcaactattg gtttatgaat acagaacgca tgcagagcat ggataaagtg | 480 |
| aatgtgtaca atgaaagcat ttatatgctg accaaaattg gcttccgctg ggccggtatc | 540 |
| attcagaccc tgaagaggc cgagcagaat gccaagacaa tggacaccat gatcaacagc | 600 |
| tttgtgagcc tgggcagcgc ctacaagggt tacaaaaaag ccaagaaagc ccgcaagcgc | 660 |
| gtggaagatt ttctggagaa acaaattatc gacgttcgta aaggcaaact gcatccggag | 720 |
| gaaggtaccg ccctgtacga attcgcccat tgggaagacc tgaacgataa cccgatggac | 780 |
| agccatctgt gcgccgttga tctgatgaac gttgttcgcc cgctggcagc aattaaccgc | 840 |
| ttcattagct acgcgttaa agtgctgatc gaattcgacc aggaaaaaga aaagctgcgc | 900 |
| ctggagaaca acgaggacta cgcctacaag ttcgcacagg aagtgcgccg tatctttccg | 960 |
| ttcgtgcctt acttaccggg tcgcgccgcc gtggatctgg agtatgatgg ctataagatc | 1020 |
| ccggccggta tgatgaccgc cctggatgtt tacggtacca cacacgatga ggatctgtgg | 1080 |
| gagaatccgg atcagttcaa cccgaatcgt tttgataact gggacggcag tccgtttgat | 1140 |
| ctgattccgc agggcggtgg cgatttctac accaatcatc gttgcgccgg cgagtggatc | 1200 |
| accgtgatta ttatggaaga aacaatgaaa tactttgcca acaaaattga attcgatgtg | 1260 |
| ccgagtcagg acctgagcgt taaactggac aaactgcctg caacgtgac cagcggtacc | 1320 |
| atcattagca acgtgcgtcc gcgtgttgcc cgcaaataa | 1359 |

<210> SEQ ID NO 10
<211> LENGTH: 1275
<212> TYPE: DNA
<213> ORGANISM: Artificial Sequence
<220> FEATURE:
<223> OTHER INFORMATION: codon-optimized nucleotide sequence encoding Sm46-del29

<400> SEQUENCE: 10

| | |
|---|---|
| gcaaaaaagc tgcctaaagt gaaaggtctg gacaacaccg tggacatcat caagggtggc | 60 |
| tatacctacg tgcctggcaa actggaggag ttcgacagca agcattcga agtgcgcgcc | 120 |
| ctgggtggca gaagatcgc agtgatgagc ggcaaggaag ccgccgagat tttttatgat | 180 |
| aacgaaaaaa tggagcgtca gggtaccctg ccgaagcgca tcgtgaacac actgttcggt | 240 |
| aaaggcgcca ttcataccac cgccggcaag aaacatgtgg atcgcaaggc actgttcatg | 300 |
| agtctgatga ccgatgaaaa tttaaattat ctgcgcgaac tgacacgcaa ctattggttt | 360 |
| atgaatacag aacgcatgca gagcatggat aaagtgaatg tgtacaatga aagcatttat | 420 |
| atgctgacca aaattggctt ccgctgggcc ggtatcattc agaccctga gaggccgag | 480 |
| cagaatgcca agacatgga caccatgatc aacagctttg tgagcctggg cagcgcctac | 540 |
| aagggttaca aaaagccaa gaaagcccgc aagcgcgtgg aagattttct ggagaaacaa | 600 |
| attatcgacg ttcgtaaagg caaactgcat ccggaggaag gtaccgccct gtacgaattc | 660 |
| gcccattggg aagacctgaa cgataacccg atggacagcc atctgtgcgc cgttgatctg | 720 |
| atgaacgttg ttcgcccgct ggcagcaatt aaccgcttca ttagctacgg cgttaaagtg | 780 |

```
ctgatcgaat tcgaccagga aaaagaaaag ctgcgcctgg agaacaacga ggactacgcc      840
tacaagttcg cacaggaagt gcgccgtatc tttccgttcg tgccttactt accgggtcgc      900
gccgccgtgg atctggagta tgatggctat aagatcccgg ccggtatgat gaccgccctg      960
gatgtttacg gtaccacaca cgatgaggat ctgtgggaga atccggatca gttcaacccg     1020
aatcgttttg taactgggaa cggcagtccg tttgatctga ttccgcaggg cggtggcgat     1080
ttctacacca atcatcgttg cgccggcgag tggatcaccg tgattattat ggaagaaaca     1140
atgaaatact ttgccaacaa aattgaattc gatgtgccga gtcaggacct gagcgttaaa     1200
ctggacaaac tgcctggcaa cgtgaccagc ggtaccatca ttagcaacgt gcgtccgcgt     1260
gttgcccgca aataa                                                       1275

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
gtccatatgg caaaaaagct gcctaaagtg                                         30

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
gtactcgagt tatttgcggg caacacgcgg                                         30

<210> SEQ ID NO 13
<211> LENGTH: 424
<212> TYPE: PRT
<213> ORGANISM: Artificial Sequence
<220> FEATURE:
<223> OTHER INFORMATION: Sm46-del29

<400> SEQUENCE: 13
```

Ala Lys Lys Leu Pro Lys Val Lys Gly Leu Asp Asn Thr Val Asp Ile
1               5                   10                  15

Ile Lys Gly Gly Tyr Thr Tyr Val Pro Gly Lys Leu Glu Glu Phe Asp
            20                  25                  30

Ser Lys Ala Phe Glu Val Arg Ala Leu Gly Gly Lys Lys Ile Ala Val
        35                  40                  45

Met Ser Gly Lys Glu Ala Ala Glu Ile Phe Tyr Asp Asn Glu Lys Met
    50                  55                  60

Glu Arg Gln Gly Thr Leu Pro Lys Arg Ile Val Asn Thr Leu Phe Gly
65                  70                  75                  80

Lys Gly Ala Ile His Thr Thr Ala Gly Lys Lys His Val Asp Arg Lys
                85                  90                  95

Ala Leu Phe Met Ser Leu Met Thr Asp Glu Asn Leu Asn Tyr Leu Arg
            100                 105                 110

Glu Leu Thr Arg Asn Tyr Trp Phe Met Asn Thr Glu Arg Met Gln Ser
        115                 120                 125

Met Asp Lys Val Asn Val Tyr Asn Glu Ser Ile Tyr Met Leu Thr Lys
    130                 135                 140

-continued

```
Ile Gly Phe Arg Trp Ala Gly Ile Ile Gln Thr Pro Glu Glu Ala Glu
145                 150                 155                 160

Gln Asn Ala Lys Asp Met Asp Thr Met Ile Asn Ser Phe Val Ser Leu
                165                 170                 175

Gly Ser Ala Tyr Lys Gly Tyr Lys Lys Ala Lys Lys Ala Arg Lys Arg
            180                 185                 190

Val Glu Asp Phe Leu Glu Lys Gln Ile Ile Asp Val Arg Lys Gly Lys
        195                 200                 205

Leu His Pro Glu Glu Gly Thr Ala Leu Tyr Glu Phe Ala His Trp Glu
    210                 215                 220

Asp Leu Asn Asp Asn Pro Met Asp Ser His Leu Cys Ala Val Asp Leu
225                 230                 235                 240

Met Asn Val Val Arg Pro Leu Ala Ala Ile Asn Arg Phe Ile Ser Tyr
                245                 250                 255

Gly Val Lys Val Leu Ile Glu Phe Asp Gln Glu Lys Glu Lys Leu Arg
            260                 265                 270

Leu Glu Asn Asn Glu Asp Tyr Ala Tyr Lys Phe Ala Gln Glu Val Arg
        275                 280                 285

Arg Ile Phe Pro Phe Val Pro Tyr Leu Pro Gly Arg Ala Ala Val Asp
    290                 295                 300

Leu Glu Tyr Asp Gly Tyr Lys Ile Pro Ala Gly Met Met Thr Ala Leu
305                 310                 315                 320

Asp Val Tyr Gly Thr Thr His Asp Glu Asp Leu Trp Glu Asn Pro Asp
                325                 330                 335

Gln Phe Asn Pro Asn Arg Phe Asp Asn Trp Asp Gly Ser Pro Phe Asp
            340                 345                 350

Leu Ile Pro Gln Gly Gly Gly Asp Phe Tyr Thr Asn His Arg Cys Ala
    355                 360                 365

Gly Glu Trp Ile Thr Val Ile Ile Met Glu Glu Thr Met Lys Tyr Phe
370                 375                 380

Ala Asn Lys Ile Glu Phe Asp Val Pro Ser Gln Asp Leu Ser Val Lys
385                 390                 395                 400

Leu Asp Lys Leu Pro Gly Asn Val Thr Ser Gly Thr Ile Ile Ser Asn
                405                 410                 415

Val Arg Pro Arg Val Ala Arg Lys
                420
```